US007951607B2

(12) United States Patent
Corcoran et al.

(10) Patent No.: US 7,951,607 B2
(45) Date of Patent: May 31, 2011

(54) COMPOSITIONS AND METHODS FOR DETECTING NERVE AGENTS

(75) Inventors: Robert C. Corcoran, Laramie, WY (US); Aaron D. Strickland, Trumansburg, NY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 12/691,636

(22) Filed: Jan. 21, 2010

(65) Prior Publication Data

US 2010/0130757 A1 May 27, 2010

Related U.S. Application Data

(62) Division of application No. 11/304,067, filed on Dec. 15, 2005, now Pat. No. 7,674,627.

(60) Provisional application No. 60/636,578, filed on Dec. 16, 2004.

(51) Int. Cl.
*C07C 229/28* (2006.01)
*C07C 225/02* (2006.01)
*C07C 251/32* (2006.01)
*C07C 237/14* (2006.01)
*C07C 211/00* (2006.01)
*C07D 311/82* (2006.01)

(52) U.S. Cl. ........ 436/104; 436/103; 564/265; 564/253; 564/248; 564/1; 588/303; 588/1; 594/394; 594/200; 594/1

(58) Field of Classification Search .................. 436/104, 436/103; 549/394, 388, 385, 381, 356, 200, 549/1; 564/265, 253, 248, 1; 588/303, 388, 588/1

See application file for complete search history.

(56) References Cited

U.S. PATENT DOCUMENTS 2,926,072 A * 2/1960 Kramer et al. ................ 436/104
5,327,211 A    7/1994 Carron et al.
5,576,216 A   11/1996 Patchornik
7,674,627 B2   3/2010 Corcoran et al.

FOREIGN PATENT DOCUMENTS

WO    WO 98/59234    12/1998

OTHER PUBLICATIONS

Geier et al., Patch testing with the irritant sodium lauryl sulfate (SLS) is useful in interpreting weak reactions to contact allergens as allergic or irritant, Contact Dermitis, 2003, 48, 99-107.*
Angel et al. (1990) "Development of a Drug Assay Using Surface-Enhanced Raman Spectroscopy," *SPIE* 1201:469-473.
Akiyama et al. (1981) "Ethynologs of Triphenylmethane Dyes. Syntheses and Properties of Acetylenic Analogs of Malachite Green, Crystal Violet, and Their Related Compounds," *Chem. Lett.* :311-314.
Akiyama et al. (1987) "Triphenylmethane Dye Ethynologues with Absorption Bands in the Near I.R.," *J. Chem. Soc. Chem. Commun.* :710-711.
Cabalin et al. (1993) "Surface-Enhanced Raman Spectrometry for Detection in Liquid Chromatography Using a Windowless Flow Cell," *Talanta*, 40(11):1741-1747.
Carey et al. (1978) "Resonance Raman Labels: A Submolecular Probe for Interactions in Biochemical and Biological Systems," *Accounts of Chemical Research* 11:122-128.
Hackley et al. (1955) "Acceleration of the Hydrolysis of Organic Fluorophosphates and Fluorophosphanates with Hydroxamic Acids," *J. Am. Chem. Soc.* 77:3651-3653.
Heyns et al. (1994) "SERS Study of the Interaction of Alkali Metal Ions with Thiol-Derivatized Dibenzo-18-Crown-6," *Anal. Chem.* 66(9):1572-1574.
Hurd et al. (1954) "A Novel Rearrangement of Hydroxamic Acids Using Sulfonyl Chlorides," *J. Am. Chem. Soc.* 76:2791-2792.
Hurd et al. (1939) "Hydroxylamine," In; *Inorganic Synthesis*, vol. 1, pp. 87-89.
Jones et al. (1921) "Rearrangements of Some New Hydroxamic Acids Related to Heterocyclic Acids and to Diphenyl- and Triphenyl-Acetic Acids," *J. Am. Chem. Soc.* 43:2422-2448.
Lacey, R.J. (1997) "Some Advances in the Use of Raman Spectroscopy in Security Screening Applications," *IEE Conference Publication* 437:10-12.
Mullen et al. (Jun. 1992) "Trace Detection of Ionic Species with Surface Enhanced Raman Spectroscopy," *Spectroscopy* 7(5):24-31.
Storey et al. (1995) "Applications of Surface-Enhanced Raman Scattering (SERS) to Chemical Detection," *Spectroscopy* 10(3):20-25.
Torres et al. (Jul. 1987) "Trace Determination of Nitrogen-Containing Drugs by Surface Enhanced Raman Scattering Spectroscopy on Silver Colloids," *Anal. Chem.* 59(13):1626-1632.
Wachter et al. (1995) "Hybrid Substrates for Real-Time SERS-Based Chemical Sensors," *Appl. Spectrosc.* 49(2):193-199.
Weiberth et al. (1987) "Copper(I)-Activated Addition of Grignard Reagents to Nitriles. Synthesis of Ketimines, Ketones, and Amines," *J. Org. Chem.* 52:3901-3904.
Yale et al. (1943) "The Hydroxamic Acids," *Chem. Rev.* 33:209-256.
Zhang et al. (2003) Fluorescent Detection of Chemical Warfare Agents: Functional Group Specific Ratiometric Chemosensors, *J. Am. Chem. Soc.* 125:3420-3421.
*Inorganic Syntheses*, McGraw-Hill Book Company, Inc., vol. 1, Chapter 5, section 30, p. 87 (1939).

* cited by examiner

*Primary Examiner* — Walter D Griffin
*Assistant Examiner* — Christine T Mui
(74) *Attorney, Agent, or Firm* — Greenlee Sullivan P.C.

(57) ABSTRACT

The present invention provides methods and compositions for detecting, identifying and measuring the abundance of chemical nerve agents. Methods and compositions of the present invention are capable of providing selective detection of phosphorous based nerve agents, such as nerve agents that are esters of methyl phosphonic acid derivatives incorporating a moderately good leaving group at the phosphorus. Selectivity in the present invention is provided by a sensor composition having an alpha ($\alpha$) effect nucleophile group that undergoes specific nucleophilic substitution and rearrangement reactions with phosphorus based nerve agents having a tetrahedral phosphorous bound to oxygen. The present invention includes embodiments employing a sensor composition further comprising a reporter group covalently linked to the alpha effect nucleophile group allowing rapid optical readout of nerve agent detection events, including direct visual readout and optical readout via spectroscopic analysis.

8 Claims, 2 Drawing Sheets

COMPOSITIONS AND METHODS FOR DETECTING NERVE AGENTS

CROSS-REFERENCE TO RELATED APPLICATIONS

This application is a divisional of U.S. patent application Ser. No. 11/304,067, filed on Dec. 15, 2005, which claims priority under 35 U.S.C. 119(e) to U.S. provisional Patent Application 60/636,578 filed Dec. 16, 2004, which is hereby incorporated by reference in its entirety to the extent not inconsistent with the disclosure herein.

STATEMENT REGARDING FEDERALLY SPONSORED RESEARCH OR DEVELOPMENT

This invention was made, at least in part, with United States governmental support awarded by National Institutes of Health Grant No. CC47900. The United States Government has certain rights in this invention.

BACKGROUND OF INVENTION

The present invention pertains to methods and compositions providing rapid, sensitive and specific detection of chemical warfare nerve agents. Chemical warfare agents are divided into a number of classes, the most prominent of which are vesicants and nerve agents. The former category includes sulfur and nitrogen "mustards" that typically incorporate 2-haloethylsulfide or 2-haloethylamine units. These compounds are often termed "blistering" agents, and are both strong alkylating agents and sources of localized hydrochloric acid. Incapacitation (and eventual death) may occur with topical exposure, but they are most effective when inhaled, due to rapid lung damage.

Though vesicants were used with horrifying effect in the First World War and more recently in Iraq, their utility as weapons and terror agents pale in significance when compared to nerve agents. Scheme 1 provides structures of several specific nerve agents and a generalized structure typical of all common nerve agents. These compounds, exemplified by sarin (isopropyl methylfluorophosphonate), share a common structural motif: they are esters of a methyl phosphonic acid derivative that incorporates a moderately good leaving group at phosphorus. It is important that the leaving group is only moderately good, as premature hydrolysis by water will occur with good leaving groups (e.g., chloride, bromide). The utility of nerve agents stems from their extraordinary toxicity; a lethal dose can be as little as 0.01 mg/kg in man (<2 mg for most adults).

Nerve agents act by inhibiting the enzyme acetylcholinesterase, and their design can be understood on this basis. Muscular contraction is initiated by release of the neurotransmitter acetylcholine across a synaptic junction. If the acetylcholine is not somehow removed, a continuous AON@ signal to the muscles will be delivered, resulting in paralysis. Acetylcholinesterase accomplishes this removal by hydrolyzing the ester linkage to give acetate and choline (which is later recycled). The acetylcholine is bound in an active site that includes a hydrophobic pocket for the ethyltrimethylammonium group and a hydrogen bond donating group for the acetyl carbonyl. Attack by an active site serine residue leads to a key tetrahedral intermediate that breaks down to give an acetylated serine residue and choline. Loss of choline is followed by enzymatically mediated attack by water as a nucleophile, to again form a tetrahedral intermediate that breaks down to give acetate and the original serine residue. The key catalytic action of the enzyme involves facilitating the formation of tetrahedral intermediates involving the active site serine residue.

Nerve agents combine the features of active site directed reactive agents and transition state analogs. Binding of the nerve agent in the active site of acetylcholinesterase is enhanced by interaction of the alkyl group of the ester with the hydrophobic binding pocket of the enzyme, and by the interaction of the phosphoryl oxygen with a hydrogen bonding group. Reaction with the serine hydroxyl gives a phosphonate ester. Importantly, this phosphonate ester closely resembles the tetrahedral intermediate that the enzyme is designed to stabilize. Though the carbon based tetrahedral intermediate formed in the natural enzymic reaction is inherently unstable, this is not the case for the phosphonate ester; this serine phosphonate ester is quite stable, and is not subject to ready hydrolysis. As a result, the enzyme is left in a condition in which the serine residue is tied up as an ester, with the active site blocked. No further catalytic action can take place, and any acetylcholine released by nerve cells is not degraded, leading to a permanent "on" state of muscular contraction. From this description, it may be seen that the essential features of a nerve agent are simply a tetrahedral phosphorous having a P=O bond and a leaving group, leading to the generalized formula: XYP(O)MLG (see, Scheme 1 for the corresponding generalized structure). The other groups V and L attached to the phosphorous should not be so large as to interfere with binding to the enzyme, but there is considerable latitude with respect to the actual identities; not only may their size vary, but they may be alkyl, ester or dialkylamide groups (e.g., Tabun).

Scheme 1: Examples of specific nerve agents and a generalized structure typical of all common nerve agents.

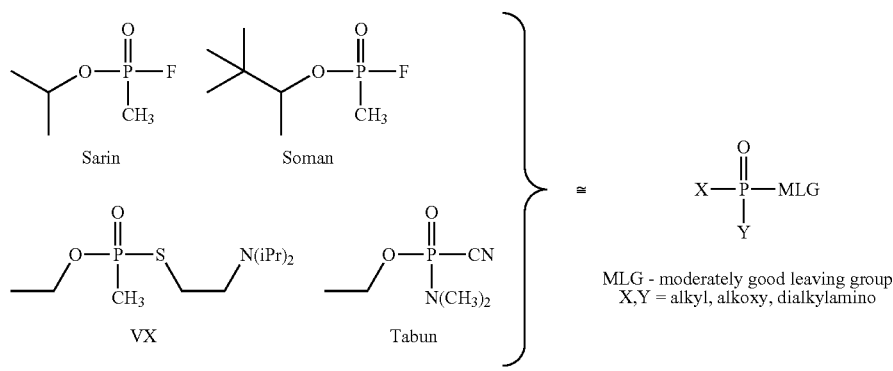

The threat posed by nerve agents has made them important targets for detection. Analytical methods employed have included gas-chromatography-mass spectrometry, HPLC methods with various detection systems (e.g. UV, refractive index, post-column derivatization) and capillary electrophoresis. More novel methods include those based on biosensors and immunoassays. Many of these methods are excellent for the purpose of retrospective analysis; that is, for examining a site and determining whether nerve agents have been used recently or relatively long ago (i.e., methods that focus on detecting nerve agent degradation products). However, most of these methods require instrumentation that is emphatically non-portable, quite expensive, and which is not well suited to the rapid analysis of multiple samples—or the even more attractive goal of continuous or near-continuous real-time analysis.

All of the analytical methods described above share an additional disadvantage: they are specific to the molecular identity of the nerve agents subject to detection. Analytical techniques typically begin with the separation of the components of a sample matrix (e.g., by HPLC, GC, TLC, CE). In the simplest analytical methods identification is made on the basis of elution time (or elution distance, in the case of TLC), while more sophisticated methods couple this time information with spectral identification (e.g., molecular mass, redox potential, etc.). Unfortunately, the very specificity of these methods may lead to a false sense of security; if either the elution time of a substance or the characteristic spectral signature of the compound is different than what has been defined for a target nerve agent, then the compound will not be identified as a threat. Yet, it may still be a threat. A somewhat facetious example of this would be the use of $d_3$-sarin, $CD_3P(O)(O-iPr)F$. When analyzed by GC-MS, this compound would have an essentially identical retention time as sarin, but would not be identified as such, since its mass would differ; it would simply be considered to be some harmless, co-eluting impurity. A more realistic example would be the use of a less common ester of a methylfluorophosphonate (e.g., $CH_3P(O)(OEt)F$), or a phosphinate ester (e.g., $CH_3iBuP(O)F$, the isostere of sarin); while it is true that compounds like these will not be quite as effective as sarin or soman, they will nevertheless provide a high killing rate.

As pointed out above, the essential features of a nerve agent are a tetrahedral phosphorus with a P=O bond and a moderately good leaving group; one need only look at the similar effectiveness of Sarin, Soman and Tabun and their structural diversity with respect to leaving group and other phosphorous substituents (See, e.g. Scheme 1) to realize that simple permutations around phosphorous will lead to a multitude of nerve agents, all having unique retention times by various separations methods, and all having unique spectral signatures. Some of the analytical methods described above could be adapted to the detection of this multitude of compounds (e.g., GC-MS) at the cost of developing and maintaining an extensive and sophisticated library of retention times and spectral signatures. However, in many of the methods (e.g., the highly specific immunoassays), even this would be impractical; scores of individual tests would have to be run.

In sum, the bulk of the analytical methods available for nerve agents are politically useful, for the purpose of determining whether an enemy (or potential enemy) has tested or used specific, known nerve agents. However, the bulk and power requirements of most of the instruments employed make them impractical for battlefield conditions, and in the rare cases where this is not a problem, they are often incapable of detecting the presence of substances that can act as nerve agents rapidly enough to avoid exposure. Finally, these analytical methods share the common limitation that they can only detect compounds that are expected, whereas in a practical sense it doesn't matter if troops are going to be killed by the most sophisticated and "popular" nerve agent available; what matters is that they are being exposed to a rapidly acting acetylcholinesterase inhibitor, and that substance may differ from those commonly detected through convenience (i.e., ready manufacture), or more chillingly, by purposeful design to elude standard detection methods. Clearly, it would be desirable to have an analytical method that could rapidly detect substances that can act as nerve agents regardless of their exact structures, and which could accomplish this feat using instrumentation that was compact, robust and easily powered—or utilize no instrumentation at all.

SUMMARY OF THE INVENTION

The present invention provides methods and compositions for detecting, identifying and measuring the abundance of chemical nerve agents. Methods and compositions of the present invention are capable of providing selective detection of phosphorous based nerve agents, such as nerve agents that are esters of methyl phosphonic acid derivatives incorporating a moderately good leaving group at the phosphorus. Selectivity in the present invention is provided by a sensor composition having an alpha (α) effect nucleophile group that undergoes specific nucleophilic substitution and rearrangement reactions with phosphorus based nerve agents having a tetrahedral phosphorous atom bound to an oxygen atom, wherein the phosphorous atom has a formal double bond with the oxygen atom. The present invention includes embodiments employing a sensor composition further comprising a reporter group covalently linked to the alpha effect nucleophile group allowing rapid optical readout of nerve agent detection events, including direct visual readout and optical readout via spectroscopic analysis.

In contrast to conventional detection methods, the present methods and compositions are not limited to detecting target nerve agents having preselected, specific molecular compositions. Rather, the methods and compositions of the present invention are capable of detecting a broad class of molecules exhibiting the specific chemical reactivity critical to the bioactivity of phosphorous based nerve agents (i.e reactivity with acetylcholinesterase). Thus, the present methods are specific for detecting nerve agents exhibiting this characteristic reactivity and, are not limited to methods of detecting nerve agents having a specified molecular composition(s). Despite this inherent versatility, the present methods and compositions are highly selective and, thus, are not susceptible to false positive detection events arising from common interferents, such as phosphorous based pesticides, simple phosphate and phosphonate esters, and (for some analytical methods) simple acids. Methods and compositions of the present invention also provide rapid (e.g. a few seconds to a few minutes) and sensitive detection and/or identification of nerve agents at concentrations as low as 100 parts per billion. In addition, the present nerve agent detection methods are highly portable and do not require the extensive bulk and power requirements of many conventional mass spectrometric, chromatographic and/or mobility based detection techniques. Accordingly, methods and compositions of the present invention are compatible with a wide range of field settings including those encountered in battlefield and remote sensing applications.

In one aspect, the present invention provides a method for detecting the presence of and/or identifying a phosphorous based nerve agent using a sensor composition comprising an alpha effect nucleophile group. In an embodiment useful for sensing this broad class of nerve agents, a sensor composition comprising an alpha effect nucleophile group is provided and reacted with a phosphorous based nerve agent. The nerve agent undergoes a nucleophilic substitution reaction with the alpha effect nucleophile group of the sensor composition resulting in formation of detectable reaction product that is subsequently detected, thereby providing detection of the presence of the nerve agent. In an embodiment of the present invention providing enhanced selectivity, the present methods further comprise the step of measuring the rate of formation of the detectable reaction product. A larger observed reaction rate corresponds to a detection event involving a nerve agent and a smaller observed reaction rate may be attributable to reaction with an interferent. This aspect of the present invention provides a means of distinguishing between compositions that represent significant threats and those that do not.

In this aspect of the present invention, the detectable reaction product may be detected by any method known in the art including, but not limited to, mass spectrometry; UV-Visible spectroscopy; infrared spectroscopy; microwave spectroscopy, fluorescence spectroscopy; Raman spectroscopy; surface enhanced Raman scattering spectroscopy, chromatography (e.g. HPLC, TLC, capillary electrophoresis or GC), electrochemical analysis and ion mobility spectroscopy. For example, the formation of a detectable reaction product may be identified by detecting a change in a spectral property associated with formation of the reaction product, such as an increase or decrease in absorption, scattering or extinction at one or more selected wavelengths in UV, visible, infrared and/or microwave regions of the electromagnetic spectrum, or an observation of fluorescence, phosphorescence, chemiluminescence and/or scattering at specified wavelengths, or by measuring another property that serves to identify the formation of the detectable reaction product such as measurement of the mass-to-charge ratio, molecular mass, retention time, elution distance and/or redox potential of the detectable reaction product or derivative/fragment thereof.

A nucleophilic oxygen or nitrogen that is directly bonded to a second nitrogen, oxygen (and less commonly halide, phosphorus or sulfur) is commonly referred to as an alpha effect nucleophile. Alpha effect nucleophiles and phosphate and phosphonate esters react selectively and efficiently to form adduct reaction products that may be stable under certain conditions, or in the case of certain subclasses of alpha effect nucleophiles, may spontaneously undergo rearrangement reactions. The rapid and specific reactions between alpha effect nucleophiles and phosphate and phosphonate esters provides the basis of the selectivity and sensitivity of the present methods of detecting phosphorous based nerve agents. In the present methods, an alpha effect nucleophile group of the sensor composition selectively displaces the moderately good leaving group attached to the tetrahedral phosphorous to produce an adduct having the nucleophilic atom of the alpha effect nucleophilic group of the sensor composition directly attached to a tetrahedral phosphorous that is additionally attached to an oxygen, an ester group, and one other group. In preferred embodiments of the present invention, the adduct formed via nucleophilic substitution reaction undergoes rapid, spontaneous rearrangement to form a detectable reaction product, wherein the precise rearrangement pathway and composition of the detectable reaction product depends, at least in part, on the composition of the alpha effect nucleophile group of the sensor composition. In one embodiment, for example, the adduct undergoes rearrangement to form a non-phosphorylated detectable reaction product, such as amine, amide, nitrile, carbamate and/or carbocation reaction products.

In some embodiments, nucleophilic substitution generates a phosphorylated adduct that is stable and itself comprises a detectable reaction product. In a preferred embodiment providing enhanced selectivity, however, the adduct product formed undergoes one or more spontaneous rearrangement reactions resulting in generation of a detectable reaction product. As the adduct rearrangement pathway is strongly dependent on the composition of the alpha effect nucleophile, selection of an appropriate alpha effect nucleophile group provides a means of controlling rearrangement to stable detectable reaction products that provides additional detection specificity in the present methods. Furthermore, embodiments of the present invention employing adduct rearrangement are useful for providing fast, sensitive and reproducible readout of nerve agent detection events. In methods and compositions of the present invention employing optical readout, for example, adduct rearrangement may be accompanied by a measurable change in the optical properties of the system, for example by transforming the sensor composition or derivative thereof into a material that absorbs strongly in a selected region of the electromagnetic spectrum or by causing a significant shift in the optical characteristics of the sensor composition or derivative thereof.

In useful methods of the present invention the adduct generated by nucleophilic substitution reaction undergoes one or more rearrangement reactions, for example, a Beckmann rearrangement reaction, a Lossen rearrangement reaction, or an abnormal Beckmann reaction.

Any alpha effect nucleophile group capable of undergoing nucleophilic substitution with phosphorus based nerve agents and, optionally subsequent rearrangement reaction(s), resulting in generation of stable detectable reaction products is useable in methods and sensor compositions of the present invention. Selection of the composition of the alpha effect nucleophile is important in the present methods because it determines, at least in part, the specific reaction pathway and composition of the detectable reaction product(s) generated by rearrangement reactions of the adduct. In one embodiment wherein the adduct reaction product spontaneously undergoes rapid rearrangement via a selected, specific rearrangement pathway, the alpha effect nucleophile group comprises two heteroatoms (i.e. atoms other than C or H, typically O, S, N or P) covalently bonded to each via a relatively weak bond (e.g. a dissociation energy less than about 80 kcal mol$^{-1}$). Preferably for some embodiments, rearrangement of the adduct involves spontaneous loss of a good leaving group via a mechanism involving cleavage of the covalent bond between the two heteroatoms comprising the alpha effect nucleophile, with the leaving group being a weak base, such as a base having a conjugate acid with a $pK_a$ less than or equal to about 5. In another embodiment wherein the adduct reaction product spontaneously undergoes rapid rearrangement via a selected, specific rearrangement pathway, the alpha effect nucleophile group of the sensor composition comprises a nitrogen atom bound to an oxygen atom and a carbon atom, wherein the carbon atom is in an $sp^2$ hybridization state. Useful Alpha effect nucleophile groups of this embodiment of the invention include, but are not limited to, oximes, salts of oximes, hydroxamic acids, and salts of hydroxamic acids.

In another aspect, the present invention provides methods of detecting phosphorus based nerve agents using a sensor composition further comprising a reporter group covalently linked to the alpha effect nucleophile group for providing fast and sensitive optical readout of detection events. In one embodiment, nucleophilic substitution reaction between the alpha effect nucleophile and the nerve agent generates an adduct which undergoes a rearrangement reaction resulting in a change in the composition of the reporter group or derivative thereof that generates a measurable change in at least one spectral property of the reporter group. Useful adduct rearrangement reactions for this aspect of the invention include rearrangement reactions, such as Beckmann rearrangement reactions, Lossen rearrangement reactions, or abnormal Beckmann reactions and combinations of these if the sensor composition contains both oxime and hydroxamic groups. Another useful rearrangement reaction is that occurring upon phosphorylation of a peracid or an organic peroxyacetal. Methods of this aspect of the invention further comprise the step of detecting, identifying and/or measuring the change in the spectral property of the reporter group, thereby providing detection of the presence of the nerve agent. Useful spectral properties of the reporter group that may undergo a measurable change upon adduct formation and rearrangement include changes to the absorption spectrum (e.g. extinction coefficients at selected wavelengths or wavelength of maximum absorption for a given absorption band) in visible, UV, infrared and/or microwave regions of the electromagnetic spectrum, changes to the fluorescence excitation spectrum (e.g. excitation wavelength(s)), changes to the fluorescence emission spectrum (e.g. emission wavelength(s)) and changes to the Raman spectrum (e.g. rotational Raman spectrum and/or vibrational Raman spectrum). Sensor compositions serving the basis of this aspect of the present detection methods may be designed to provide enhanced selectivity with respect to the detection of phosphorus based nerve agents without interference from inteferents.

In an embodiment of the present invention providing optical readout of detection events by visual or spectroscopic analysis techniques, rearrangement of the adduct generated by nucleophilic substitution reaction modifies the optical properties of a reporter group or derivative thereof. For example, the present invention provides nerve agent sensing methods using a sensor composition further comprising a reporter group comprising a chromophore having a conjugated π-system covalently linked to an alpha effect nucleophile group. In this embodiment, the composition of the alpha effect nuceophile group, reporter group or both is selected such that an adduct is formed via nucleophilic substitution reaction that spontaneously undergoes a rearrangement reaction that replaces the electron withdrawing alpha effect nucleophile group with a group that is less electron withdrawing (e.g. the Hammett $\sigma_p$ value of the group is less than the Hammett $\sigma_p$ value of the alpha effect nucleophile group). In some embodiments, the alpha effect nucleophile group is replaced with a group that is electron donating. Replacement of the electron withdrawing alpha effect nucleophile group covalently linked to the reporter group with a group having different electron withdrawing properties, particularly with an electron donating moiety, strongly affects the excitation energies of excited electronic states associated with the conjugated π-system in a manner that generates a measurable change in the spectral properties (e.g. shifting of the wavelength corresponding to an absorption maximum of a given absorption band or changing the extinction coefficients at selected wavelengths) of the chromophore comprising the readout group. In some embodiments it is preferable that the composition and linkage of alpha effect nucleophile and reporter groups are selected such that rearrangement reaction replaces the alpha effect nucleophile group with a functional group selected from the group consisting of an amine group, a carbamate, a urethane, and an amide group.

Selection of an appropriate alpha effect nucleophile group and reporter group pair and means of linking these groups is important in the present invention for realizing a change in the spectral properties of the reporter group or derivative thereof that is easily detected or measured either visually or using spectroscopy analysis techniques. In a useful embodiment of this aspect of the invention, for example, the alpha effect nucleophile is a hydroxamic acid, salt of a hydroxamic acid, or an oxime or a salt of an oxime, and the conjugated π-system is directly linked to the alpha effect nucleophile by a covalent bond to the $sp^2$ hybridized carbon atom of the hydroxamic acid, salt of a hydroxamic acid, or to the $sp^2$ hybridized carbon atom of the oxime or a salt of an oxime. Useful reporter groups for this aspect of the present invention comprise dyes exhibiting significant absorption in the visible region of the electromagnetic spectrum, and include, but are not limited to, azo dyes, xanthene dyes such as an azo dye, an anthraquinone dye a xanthene dye such as pyronin or a rhodamine or a fluorescine dye, azine dyes such as neutral red and safranin, oxazine dyes such as Nile Blue, thiazine dyes such as methylene blue, triarylmethane dyes such as Malchite green, and a diarylmethane dye such as auramine. Preferably for some applications, the reporter group further comprises an electron withdrawing moiety or an electron donating moiety covalently linked to the conjugated π-system at a region of the reporter group that is distal to the alpha effect nucleophile. Incorporation of an electron withdrawing moiety or electron donating in this position in certain methods of the present invention increases the magnitude/extent of the observed change in the spectral property (or properties) of the reporter group, thereby significantly enhancing the overall sensitivity of the nerve agent detection methods.

In another embodiment of the present invention providing optical readout of detection events by visual or spectroscopic analysis techniques, rearrangement of the adduct generated by nucleophilic substitution reaction transforms a reporter group that does not significantly absorb visible light into a chromophore (i.e. material that significantly absorbs light of the visible region of the electromagnetic spectrum). For example, the present invention provides nerve agent sensing methods using a sensor composition further comprising an interrupted conjugated π-system comprising at least two spatially separated conjugated π-systems. In this embodiment, the composition of the alpha effect nuceophile group, reporter group or both is selected such that an adduct is formed via nucleophilic substitution reaction with a phosphorous based nerve agent that spontaneously undergoes a rearrangement reaction that transforms the interrupted conjugated π-system into a continuous, non-interrupted, single conjugated π-system. Formation of a continuous, non-interrupted, single conjugated π-system in this embodiment of the present invention transforms the reporter group or derivative thereof into a chromophore (e.g. a dye) that absorbs visible light significantly. In some embodiments of this aspect, a rearrangement reaction initiated by nucelophilic substitution transforms the reporter group or derivative thereof to a dye selected from the group consisting of: azo dyes, xanthene dyes, anthraquinone dyes, xanthene dyes, acridine dyes, azine dyes, oxazine dyes, thiazine dyes, triarylmethane dyes, diarylmethane dyes, quinoline styryl dyes, phthalocyanine dyes and polyalkene dyes.

In an embodiment of this aspect of the present invention the reporter group further comprises an insulating carbon atom having a $sp^3$ hybridization state positioned between at least two spatially separated conjugated π-systems, and preferably for some applications in a position that separates three conjugated π-systems. The insulating carbon atom of this embodiment is also covalently linked to the carbon atom that incorporates the alpha effect nucleophile (e.g., the sp² carbon of an oxime or hydroxamic acid). The compositions of alpha effect nucleophile group, reporter group or both are selected in this embodiment such that rearrangement reaction of the adduct product of the nucleophilic substitution reaction oxidizes the insulating carbon by replacing a C—C bond with carbon with an empty p orbital resulting in a change in hybridization state from sp³ to a sp² hybridization state, or by replacing the C—C bond by a C—N bond that is subject to ready solvolytic cleavage reaction, thereby forming a carbon with an empty p orbital, resulting in a change in hybridization state from sp³ to sp². This transformation results in formation of a non-insulating carbon that is capable of donating a p-orbital to the separated conjugated π-systems, thereby forming a continuous, non-interrupted, single conjugated π-system that exhibits spectral properties of a chromophore. For example, rearrangement reaction in some embodiments of the present invention generates a dye, such as a xanthene dye (e.g. a pyronin dye, a rhodamine dye), a triarylmethane dye (e.g. malchite green), a diarylmethane dye (e.g. auramine), and carotene.

Some methods of the present invention further comprising the step of providing a plurality of sensor compositions, wherein the sensor compositions are bound to a polymer by tethering subunits that link the reporter groups of the sensor compositions to the polymer. In some embodiments, tethering subunits are sufficiently small such that the sensor compositions are not able to interact with each other.

In another aspect, the present invention provides compounds for detecting, sensing, identifying and measuring the abundance of phosphorus based nerve agents. Sensor compounds of the present invention include hydroxamic acids (and salts, enantiomers, fragments, and derivatives thereof) and oximes (and salts, enantiomers, fragments and derivatives) thereof. Useful hydroxamic acids and oximes are indirectly or directly linked to functional groups having one or more conjugated π-systems, including one or more aromatic or substituted aromatic rings, one or more heteroaromatic or substituted heteroaromatic rings, one or more functional groups comprising at least two atoms chosen from carbon and nitrogen that are doubly or triply bonded to each other, and/or one or more functional groups selected from the group consisting of hydrogen, alkyl, aryl, heteroaryl, alkenyl, alkynyl, as well as halide, alkoxyl, arylaoxy, alkyl- or aryl- or dialkyl- or diaryl- or alkylarylamino, thioalkyl, or thioaryl.

In one embodiment, sensor compounds of the present invention have the structure G1 comprising an alpha effect nucleophile group linked to a reporter group.
G1: Structure for Sensor Compounds of the Present Invention.

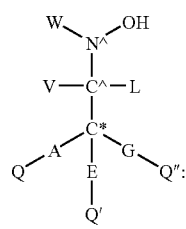

The definitions of W, V, L, A, E, G, Q, Q', and Q" functional groups follow below. Throughout the present description, the use of the asterix (*) and up carrot (ˆ) carrot designations in the present chemical structures is a convention for enhancing clarity by referring to carbon and nitrogen atoms having specific positions in exemplary compositions of the present invention.

L is an alkyl or aryl group, or substituted alkyl or aryl group. In one class of embodiments W is H, with V and L the identical oxygen atom (that is, Cˆ=O), to give a hydroxamic acid. In another class of embodiments, W and V are the same bond, which gives a double bond between Cˆ and Nˆ, with L as an alkyl or aryl group, or substituted alkyl or aryl group. Most preferably in this case, L is methyl, but it may also be alkyl, aryl, or substituted alkyl/aryl (and heteroaryl/substituted heteroaryl). In this case, the structure represents an oxime.

In an embodiment, the present invention comprises a class of molecules having an alpha effect nucleophile group comprising a hydroxamic acid functional group (or salt, enantiomer, fragment or derivative thereof). Compounds of this aspect of the present invention have the structure G2.
G2: Structure of Sensor Compound Having a Hydroxamic Acid Functional Group.

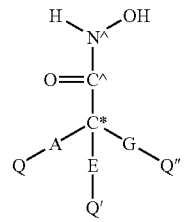

In another embodiment of this aspect of the present invention, the present invention comprises a class of molecules having an alpha effect nucleophile group comprising an oxime functional group (or salt, enantiomer, fragment or derivative thereof). Compounds of this aspect of the present invention have the structure G3.
G3: Structure of Sensor Compound Having an Oxime Functional Group.

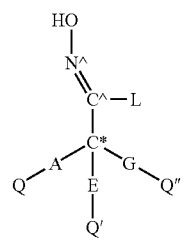

Structures G1, G2 and G3 are particularly useful in Sens$_{conj}$ methods of the present invention.

The definitions of W, V, L, C*, A, E, G and Q/Q'/Q" are the same for the structures G1, G2, G3, G4, G5 and G6.

C* in G1, G2, G3 (and G4, G5 and G6 below) refers to an "insulating" carbon. In one embodiment, this carbon has an sp³ hybridization state prior to reaction of the sensor compound with a nerve agent. In the course of a reaction-rearrangement sequence this carbon is transformed to a sp² hybridization state.

The functional group A constitutes a conjugated π-system directly attached to C* that is comprised of at least four atoms chosen from carbon and nitrogen having sp² or sp hybridization that are connected in an uninterrupted fashion, and geometrically oriented such that there is substantial overlap between any adjacent pair of p-orbitals. Most commonly, the group A will be an aromatic or substituted aromatic ring, or a heteroaromatic or substituted heteroaromatic ring. The group A may optionally be additionally attached to one or more examples of a group Q, the definition of which is given below.

The functional group E may be defined in the same way as G, below, but will preferably comprise at least two atoms chosen from carbon and nitrogen that are doubly or triply bonded to each other, with at least one bond from these atoms directly to C*. More commonly, E will comprise two to thirty atoms chosen from carbon or nitrogen atom having sp or $sp^2$ hybridization that are in an uninterrupted sequence such that each atom is adjacent to at least one other in the sequence, and possessing geometries about each atom that allows for the substantial overlap of a p-orbital of one atom with an adjacent member of the two to thirty atoms, thereby forming what is commonly considered to be a conjugated π-system. This conjugated π-system may be optionally substituted by one or more groups Q', the definition of which is given below.

The functional group G may include hydrogen, alkyl, aryl, heteroaryl, alkenyl, alkynyl, as well as halide, alkoxyl, aryloxy or aroyloxy, alkyl- or aryl- or dialkyl- or diaryl- or alkylarylamino, thioalkyl, or thioaryl. The group G may also be optionally substituted by a group Q", the definition of which is given below. In cases in which the atom of G that is directly attached to C* is oxygen, nitrogen, or sulfur it may be particularly beneficial to have the group Q" such that it is attached to another portion of G or to A or E, so as to reduce hydrolytic lability of the reaction-rearrangement product.

Optionally, each of the groups A, E and G may be substituted with one or more substituents Q, Q' and Q". It is important to note that present invention includes compositions having structures G1, G2 or G3 without one or more of substituents Q, Q' and Q". These substituents (Q, Q' and Q") may comprise atoms or groups of atom that have electron donating or electron withdrawing characteristics such that they modify the spectral characteristics of the dye-like product of the reaction-rearrangement sequence or the solubility of the sensor in water or other solvents. Thus, these electron donating or electron withdrawing groups may include halogens, —OR, —SR, —NRR', —C(O)R, —C(O)H, —COOR, —CN, —CR=NR', —C(O)NRR', —NO$_2$, —NO, —N=NR, —N$^+$RR'R", —S(O)R, —SO$_2$R, —SO$_3^-$, —P(O)(OR)(OR'), —P(O)(NRR')OR", in which R, R' and R" are independently H, alkyl or aryl, and where it should be understood that when R is H and attached to oxygen, nitrogen or sulfur the possibility that this proton is lost under the conditions of the assay to give the conjugate base is an allowable possibility, and may even be desirable. Examples of Q that would tend to increase water solubility would include —OR (especially including —OH, —O$^-$ and polyethers such as polyethylene glycol and polypropylene glycol ethers), —NRR' (provided the R/R' groups themselves are substituted so as to promote water solubility), —C(O)R, —N$^+$RR'R", —S(O)R, —SO$_2$R, —SO$_3^-$, —P(O)(OR)(OR'), —P(O)(NRR')OR", in which R, R' and R" are independently H, alkyl or aryl, and where it should be understood that when R is H and attached to oxygen, nitrogen or sulfur the possibility that this proton is lost under the conditions of the assay to give the conjugate base is an allowable possibility, and may be desirable.

Optionally, each of the groups Q, Q' and Q" may and independently constitute a group having an affinity for one or more solid matrices. These solid matrices may include, but are not limited to silica gel, alumina, diatomaceous earth, clay, powdered carbon, ion exchange resins, silver, gold, copper or other metals, including colloidal metal and nanoparticle metal compositions. In these applications, a group Q, Q' or Q" will most commonly include one or more of a highly polar group such as —COOR, —N$^+$RR'R", —SO$_3$R, —P(O)(OR)(OR'), —P(O)(NRR')OR", in which R, R' and R" are independently H, alkyl or aryl, and where it should be understood that when R is H and attached to oxygen, nitrogen or sulfur the possibility that this proton is lost under the conditions of the assay to give the conjugate base is an allowable possibility, and may even be desirable. Alternatively, the matrix may comprise a hydrophobic polymer, in which case one or more of Q, Q' or Q" will comprise a hydrophobic group such as aromatic, alkyl, or alkyl or aryl substituted silicon or sulfur.

In some embodiments, any combination of functional group A, functional group E, and functional group G are connected by functional group Q, functional group Q', functional group Q" or any combination of these.

In some embodiments, one or more of Q, Q' or Q" substituents is covalently attached to a solid support. Such solid supports include, but are not limited to silica gel, glass, polymers, silver, gold, copper, or other metals, and also include colloidal metal and nanoparticle metal compositions. Covalent attachment to silica gel or glass will most commonly be accomplished by having an —Si(OR)$_3$ or —Si(halide)$_3$ group terminating an alkyl or polyether chain. Covalent attachment to a metal, colloidal metal or nanoparticle metal surface will most commonly be accomplished by having an —SR, —SeR, or disulfide or diselenide group terminating an alkyl, aryl or polyether chain. One skilled in the art will recognize that there are a multitude of functionalized polymers and corresponding methods for attaching groups to those polymers, and an exhaustive list is not given here. The most common polymers that might be employed would include, but not be limited to functionalized polystyrenes and functionalized polyethylenes, and the attachment to these polymers include the possibilities of linkages of the type [P]—C(O)O-Q, [P]—C(O)NRQ, [P]—NRC(O)Q, [P]—CRR'OQ, [P]—CRR'NR"Q, [P]—CRR'SQ, [P]SCRR'Q, [P]—SO$_2$NRQ, [P]—N=NQ, [P]—NRSO$_2$Q, [P]—OSO$_2$Q, [P]—P(O)(OR)OQ, [P]—OP(O)(OR)OQ, [P]—OP(O)(OR)Q, in which [P]— represents a polymer, Q is also attached to the sensor as shown in the reference formula, and in which R, R' and R" are independently H, alkyl or aryl, and where it should be understood that when R is H and attached to oxygen or nitrogen the possibility that this proton is lost under the conditions of the assay to give the conjugate base is an allowable possibility, and may even be desirable.

One or more of these groups Q, Q' or Q" may also be involved in the formation of a cyclic system or systems by acting as a bridging group. Thus, a group Q, Q' or Q" that is capable of the formation of two covalent bonds might be attached to two or more atoms of a given conjugated system A, E or (when applicable) G to give a cyclic A, a cyclic E or a cyclic G. Alternatively, a group Q, Q' or Q" capable of formation of at least two covalent bonds may connect two of the groups attached to C*. For example, a group Q might be connected to both A and E, A and G, E and G or A, E, and G. When Q/Q'/Q" acts as a bridging group in these circumstances it must simply be able to form two covalent bonds (thus excluding halogens), and includes the groups —R—, —R—O—R'—, —R—S—R'—, —R—NR"—R'—, —R—C(O)—R'—, —R—C(O)OR'—, —R—C(O)NR"R'—, —RP(O)(OR")OR'—, —R—S(O)—R'—, —R—SO$_2$—R'—, where in this context, the groups R, R', and R" may be null (i.e., not present, with direct bonds being formed to the otherwise indicated atoms), alkyl, aryl, or heteroaryl. Furthermore, it is the case that on or more of the R, R' and R" groups may be additionally substituted with an additional group Q" that has the same possibilities of characteristics as defined for Q/Q'/Q".

In an embodiment, the present invention comprises sensor compositions having the structures G4, G5 and G6 having an alpha effect nucleophile group linked to a reporter group having a plurality of conjugated π-systems that comprise an interrupted π-systems.

G4: Structure of Sensor Composition.

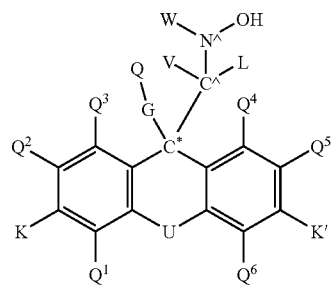

G5: Structure of Sensor Composition Having a Hydroxamic Acid Alpha Effect Nucleophile Group.

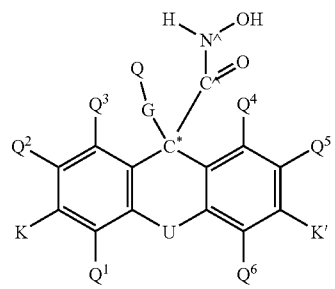

G6: Structure of Sensor Composition Having an Oxime Alpha Effect Nucleophile Group.

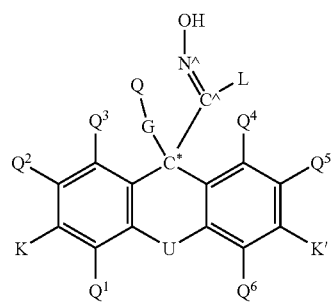

Structures G3, G4 and G5 are particularly useful in Sens$_{conj}$ methods of the present invention.

In one embodiment of compound G6 L is a methyl. In structures G4, G5 and G6, functional group G is as defined above for structures G1, G2 and G3, and functional groups Q, $Q^1$, $Q^2$, $Q^3$, $Q^4$, $Q^5$, $Q^6$, K, $K^1$, and U are defined below.

The functional group U may be null (i.e., nothing; no connection between the indicated ring at this point), or may include the groups —R—, —R—O—R'—, —R—S—R'—, —R—NR"—R'—, —R—C(O)—R'—, —R—C(O)OR'—, —R—C(O)NR"R'—, —RP(O)(OR")OR'—, —R—S(O)—R'—, —R—SO$_2$—R'—, where in this context, the groups R, R', and R" may be null (i.e., not present, with direct bonds being formed to the otherwise indicated atoms), alkyl, aryl, or heteroaryl. Furthermore, it is the case that on or more of the R, R' and R" groups may be additionally substituted with an additional group Q" that has the same possibilities of characteristics as defined for Q/Q'/Q".

The groups Q, $Q^1$, $Q^2$, $Q^3$, $Q^4$, $Q^5$, $Q^6$, and K/K' are independently defined as for Q/Q'/Q" above, including the possibility that any pair of these groups may be connected to give a cyclic system, and that such connection may include an additional group Q/Q'/Q". Most commonly, K/K' will be electron donors such as —OR, —NRR' in which R is H, alkyl, aryl or heteroaryl, with it being understood that the conjugate bases of —OR and —NRR' are included when R/R' is H.

In an embodiment, the present invention comprises compositions for sensing nerve agents having the structures G7, G8 and G9 having an alpha effect nucleophile group linked to a reporter group that undergoes a change in at least one spectral property upon reaction with a phosphorus based nerve agent.

G7, G8 and G9: Sensor Composition of the Present Invention having a Reporter Group that Undergoes a Change in at Least One Spectral Property Upon Reaction with a Phosphorus Based Nerve Agent.

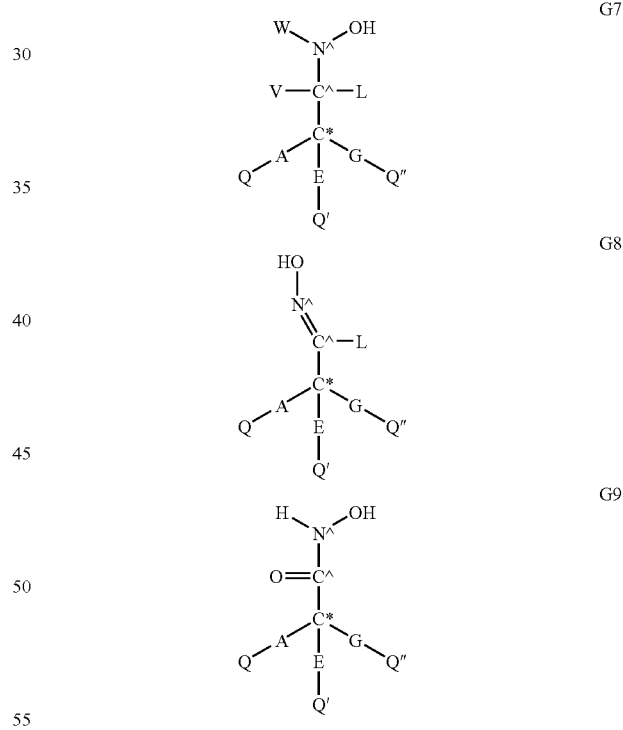

Structures G7, G8 and G9 are particularly useful in Sens$_{mod}$ methods of the present invention.

In structures G7, G8 and G9, the definitions for V, L, W and Q are as described above in the context of Structures G1, G2 and G3, while the definition of M is that it is a conjugated π-system directly attached to C^ that is comprised of at least four atoms chosen from carbon and nitrogen having sp$^2$ or sp hybridization that are connected in an uninterrupted fashion, and geometrically oriented such that there is substantial overlap between any adjacent pair of p-orbitals. The sensor molecule described must, prior to reaction with a nerve agent, have one or more absorptions in the UV-Vis spectrum in the region of 350-1200 nm in which the extinction coefficient $\epsilon$ is greater than 1,000, and is preferably >20,000. Most commonly, the group M will be an aromatic or substituted aromatic ring, or a heteroaromatic or substituted heteroaromatic ring. The group M may optionally be additionally attached to one or more examples of a group Q.

A significant benefit of the present methods for detecting phosphorous based nerve agents is that they do not rely on the specific structure of the nerve agents to be detected, but rather two aspects of their chemical reactivity with certain chemical groups incorporated into sensor molecules: firstly, their ready reactivity with what are termed alpha effect nucleophiles, and secondly the propensity of the resulting reaction products (adducts) to undergo a rearrangement reaction. Aside from the choice of the certain chemical groups as specifically appropriate alpha effect nucleophiles that will then participate in rearrangement reactions, the operation of this invention includes the additional feature that these certain chemical groups be placed on a molecular framework such that, subsequent to the rearrangement reaction, the spectroscopic characteristics of the sensor molecule as a whole undergoes a significant change. Preferably, this significant change in spectroscopic properties is a shift of the wavelength of maximum absorbance ($\lambda_{max}$) of a major band in the UV-Visible spectrum to substantially (>20 nm) higher wavelengths. In the preferred embodiments of the invention, this change in $\lambda_{max}$ will be accompanied by an increase in the extinction coefficient ($\epsilon$) for the absorption band.

In another aspect, the present invention provides a method for detecting the presence of a nerve agent comprising the steps of: (i) providing a sensor composition comprising an alpha effect nucleophile group; (ii) reacting the sensor composition with the nerve agent, wherein the nerve agent undergoes a nucleophilic substitution reaction with the alpha effect nucleophile group of the sensor composition resulting in formation of detectable reaction product; (iii) detecting the detectable reaction product, thereby detecting the presence of the nerve agent. In one embodiment of this aspect of the present invention, detectable reaction product is detected by a method selected from the group consisting of: mass spectrometry; UV-Visible spectroscopy; infrared spectroscopy; fluorescence spectroscopy; Raman spectroscopy; surface enhanced Raman scattering spectroscopy, chromatography, and ion mobility spectroscopy. Optionally, this aspect of the present invention further comprises the step of measuring the rate of formation of the detectable reaction product.

In another aspect, detection methods of the present invention uses a sensor composition further comprising a reporter group covalently linked to the alpha effect nucleophile group, wherein the nucleophilic substitution reaction between the alpha effect nucleophile and the nerve agent generates an adduct which undergoes a rearrangement reaction resulting in a change in the composition of the reporter group that generates a change in at least one spectral property of the reporter group, the method further comprising detecting the change in the spectral property of the reporter group. In one embodiment, the rearrangement reaction is selected from the group consisting of an abnormal Beckmann reaction, a Lossen rearrangement reaction, and a Beckmann reaction. In one embodiment, the spectral property of the reporter group that undergoes the change is selected from the group consisting of: the UV-Vis absorption spectrum of the reporter group, the IR absorption spectrum of the reporter group the fluorescence excitation spectrum of the reporter group, the fluorescence emission spectrum of the reporter group and the Raman spectrum of the reporter group.

DETAILED DESCRIPTION OF THE INVENTION

Figure 1:
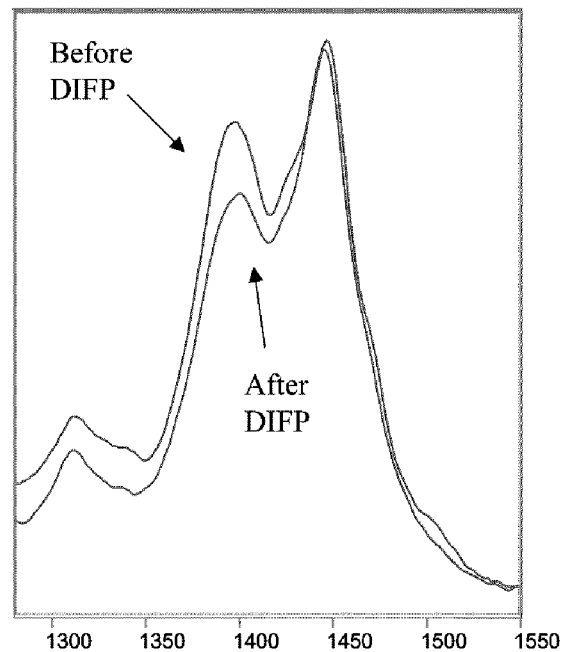
FIG. 1 provides a SERS spectra before and 3 minutes after addition of the nerve agent simulant diisopropyl fluorophosphate (DIFP) to sensor compound 12 of Example 1.

Referring to the drawings, like numerals indicate like elements and the same number appearing in more than one drawing refers to the same element. In addition, hereinafter, the following definitions apply:

"Alpha effect nucleophile group" and "α effect nucleophile group" are used synonymously in the present description and refer to a functional group having a nucleophilic atom that is directly attached either to a nitrogen atom or an oxygen (i.e. an alpha position). The nucleophilicity of the nucelophilic atom of an alpha effect nucleophile is typically at least about 100 times greater, and in some instances at least about 1000 times greater, than the nucleophilicity as predicted by a linear relationship between $\log(k/k_o)$ and $pK_a$ of the conjugate acid of a comparable non-alpha effect nucleophile, where k is the rate constant of the substitution reaction, and $k_o$ is the rate constant of a reference reaction. Alpha effect nucleophile groups useful in compositions and methods of the present invention include, but are not limited to, oximes, salts of oximes, hydroxamic acids, salts of hydroxamic acids, alkyl and aryl hydrazines, peracids, peroxyacetals or peroxyketals, and N- or O-alkyl or aryl substituted hydroxylamines.

"Conjugated π-system" refers to an uninterrupted series of p-orbitals is oriented so as to achieve at least partial overlap of the p-orbitals. Conjugated π-systems may be populated with delocalized electrons. Conjugated π-systems include linear conjugated systems, branched conjugated systems, aromatic rings and combinations of these. While, by definition, a conjugated system may not be interrupted, a more extensive conjugated system may advantageously be created by removal of an "insulating" sp$^3$ center that separates two distinct conjugated systems.

"Rearrangement," in its most technically correct sense, refers to a process in which one compound is transformed to an isomeric compound through a process involving the breaking and reforming of chemical bonds. Rearrangement reactions are typically distinguished from other processes in which a compound is transformed to an isomer by the fact that some, or all of the bond-making and bond-breaking processes occur in a simultaneous fashion. However, as is familiar to one skilled in the art, the term rearrangement also applies to reactions in which the ultimate product formed is not an isomer of the starting compound. Such a designation is commonly applied to a reaction in which a rearrangement process begins with a simultaneous bond-making/bond-breaking process to produce a reactive intermediate and a fragment from the original molecule. Recombination of the reactive intermediate with the fragment may produce a product isomeric with the starting compound (the "true," or technically correct rearrangement product), but it is quite common that the reactive intermediate may instead react with some other species present in the reaction mixture (e.g. solvent) to produce a alternative final product that is not isomeric with the starting material. Though this product is not in fact a rearranged version of the starting material, the process is nevertheless termed a rearrangement reaction because of the critically important initial simultaneous bond-breaking/bond-making process that is common to the ultimate formation of "true" rearrangement product and alternative reaction products. Examples of such processes, in which both "true" and alternative reaction products are produced in what are commonly termed rearrangement reactions, are illustrated in Scheme 2 and Scheme 3. Thus, it is commonly understood by one skilled in the art that rearrangement reactions may result in formation of a product or plurality of products that have a same molecular formula or different molecular formula than the compound that undergoes rearrangement reaction. Rearrangement reactions may involve movement or migration of a functional group or plurality of functional groups from one region of a compound to another region of a compound.

As used herein, "attached" or "linked" means two or more groups that are chemically and/or physically joined together for example by covalent bonds, ionic bonds, hydrogen bonds, coordinate covalent bonds, electrostatic interactions such as dipole-dipole interactions, hydrogen bonding and Van der Waals interactions and other forms of bonding or attraction known in the art. Attached groups may be directed attached or may be indirectly attached via a linking groups present between two or more attached groups.

"Oxime" refers to compounds having an oxime group, a salt of an oxime group (i.e. an oximate anion, with a negative charge on oxygen replacing the hydrogen of the OH), derivative of an oxime group or fragment of an oxime group. Oxime groups include compositions having the structures:

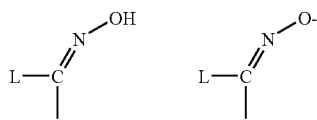

in which the two bonds to the $sp^2$ carbon indicated are to carbon atoms.

"Hydroxamic acid" refers to compounds having a hydroxamic acid group, a salt of a hydroxamic acid group (i.e. a hydroxamate, in which either or both of the NH or OH bonds are replaced by $N^-$ or $O^-$), derivative of a hydroxamic acid group or fragment of a hydroxamic acid group. Hydroxamic acid groups include compositions having the structures:

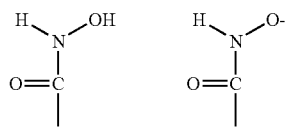

In which the remaining bond to the $sp^2$ carbon is to a carbon. Although in a broad sense hydroxamic acids include compounds in which the N—H bond may be replaced by an N—C bond, in the context of the invention here the bond will preferably be an N—H bond.

"Absorb visible light significantly" refers to materials having a molar extinction coefficient, $\epsilon$, with respect to a specified wavelength, specified wavelengths and/or in a specified region of the electromagnetic spectrum that is greater than or equal to about 1000 liters $mole^{-1}$ $cm^{-1}$.

"$Sens_{conj}$" refers to methods and compositions for detecting phosphorus based nerve agents wherein readout of a detection event is provided by conversion of a reporter group or derivative thereof from a compound or moiety that does not absorb light of a selected region of the electromagnetic spectrum, such as the visible region, significantly to a compound or moiety that does absorb light of a selected region of the electromagnetic spectrum, such as the visible region, significantly. Methods and compositions of this aspect of the present invention include, but are not limited to, readout provided by conversion of a non-dye reporter group to a dye.

"$Sens_{mod}$" refers to methods and compositions for detecting phosphorus based nerve agents wherein readout of a detection event is provided by a reporter group or derivative thereof that undergoes a change in at least one spectral property upon interaction of a sensor composition with a nerve agent. Methods and compositions of this aspect of the present invention include, but are not limited to, readout provided by a reporter group comprising a chromophore that undergoes a change in at least one spectral property upon interaction of a sensor composition with a nerve agent.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;
- —SO$_2$N(R)$_2$ where R is a hydrogen, an alkyl group, or an aryl group and R and R can form a ring;
- —OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

The present invention combines diverse features that at first glance seem incompatible: a fairly high specificity towards phosphorus based nerve agents as a class, combined with a generality of application to nerve agents, regardless of their specific structure. Accomplishing this goal, our invention, relies on the combination of at least three unrelated factors:

a) that there are certain functional groups that show unusually high chemical reactivity towards phosphate and phosphonate esters. These functional groups are called alpha effect nucleophiles. Though the unusual reactivity of this class of nucleophiles was discovered, and has been mostly studied, in the context of derivatives of carboxylic acids, they show qualitatively similar behavior with derivatives of phosphoric and phosphonic acids.

b) that, although most alpha effect nucleophiles react with esters (whether carboxylic or phosphorus based) to give stable products (adducts), a small subclass of alpha effect nucleophiles undergo spontaneous rearrangement reactions upon adduct formation with phosphorus based electrophiles.

c) that a characteristic feature of most dyes is an uninterrupted series of p-orbitals that constitutes what is termed a conjugated π-system; furthermore, the defining characteristics of a given dye molecule—the wavelength of maximum of absorbance, $\lambda_{max}$, and the extinction coefficient, $\epsilon$—can be strongly influenced by the presence of electron donating and electron withdrawing groups in positions in which they can interact with the π-system.

Alpha-effect nucleophiles. Aside from the fact that effective nerve agents must incorporate a tetrahedral phosphorous with a P=O bond, they must have a chemical reactivity that is somewhat finely tuned: if they are too reactive, they will be hydrolyzed by water or other nucleophiles present in the organism, while if they are not very reactive they will not chemically react with acetylcholinesterase, the inhibition of which causes their toxic effects. From the standpoint of detecting a nerve agent through a chemical reaction it is worth noting that many of the conditions and reagents required are relatively harsh (e.g., pH>12), leading to reaction systems that may lack long term stability (and thus reliability), or may be hazardous to transport. In most cases, there is a roughly linear logarithmic relationship between the basicity of a given type of nucleophilic atom and its reactivity towards an ester carbon (e.g., in the substitution of the alkoxy group of an ester). Thus, if one plots $\log(k/k_o)$ vs. the $pK_a$ of the conjugate acid of an oxygen nucleophile (in which k is the measured rate constant of the substitution reaction, and $k_o$ is the rate of a reference reaction), a straight line is obtained. Similar results are obtained when nitrogen nucleophiles are compared, and these reaction trends extend to phosphorus esters. On this basis, one would expect that a very basic nucleophile would be necessary to rapidly react with a nerve agent (acetylcholinesterase avoids this necessity by combining a number of interacting components in the active site). However, there are known—and now predictable—outliers to the nucleophilicity-basicity trends. Specifically, any time a nucleophilic atom is directly attached to either a nitrogen or oxygen (i.e., in the alpha position), the nucleophilicity of the nucleophilic atom is found to be much greater (typically 100- to 1000-fold) than would be predicted according to the linear relationship established for that class of atoms. Compounds of this type are called alpha-effect nucleophiles, and include hydrazine, hydrogen peroxide, hydroxylamine and all of their various derivatives. Compounds that are alpha effect nucleophiles show a similar enhanced reactivity with respect to derivatives of phosphoric and phosphonic acids, and react with nerve agents under mild conditions (i.e., near neutral pH or slightly alkaline).

Rearrangement of adducts of alpha-effect nucleophiles and nerve agents. Most alpha-effect nucleophiles react with carboxylic and phosphoric/phosphonic acid derivatives to form relatively stable substitution products. For example, hydrazine reacts to give hydrazides, and hydroxylamine reacts to give hydroxamic acids. Reaction of the hydroxamic acid with an acylating agent usually gives an adduct that is stable unless heated. However, two derivatives of hydroxylamine react with phosphoric and phosphonic acid derivatives to form unstable intermediates that undergo rearrangement reactions. Reaction of a hydroxamic acid with a phosphorylating agent (e.g., diethyl chlorophosphate, or a nerve agent) yields an unstable intermediate that undergoes what is known as a Lossen rearrangement to give a highly reactive isocyanate and a phosphoric/phosphonic acid. Scheme 2 provides a reaction scheme involving reaction of a sensor composition comprising a hydroxamic acid with a phosphorylating agent (i.e. a phosphorus based nerve agent) to give an unstable adduct that spontaneously rearranges to a phosphoric or phosphonic acid and an isocyanate, which will react in turn with other nucleophiles. While these two products can combine to give the "true" rearrangement product, more commonly the isocyanate will react with water to give an unstable carbamic acid (which can also be formed by hydrolysis of the "true" rearrangement product) that decomposes to an amine and carbon dioxide; or, the isocyanate will react with some other nucleophile (often, another hydroxamic acid) to give a carbamate or urea.

Scheme 2: Reaction of a hydroxamic acid with phosphorus based nerve agents.

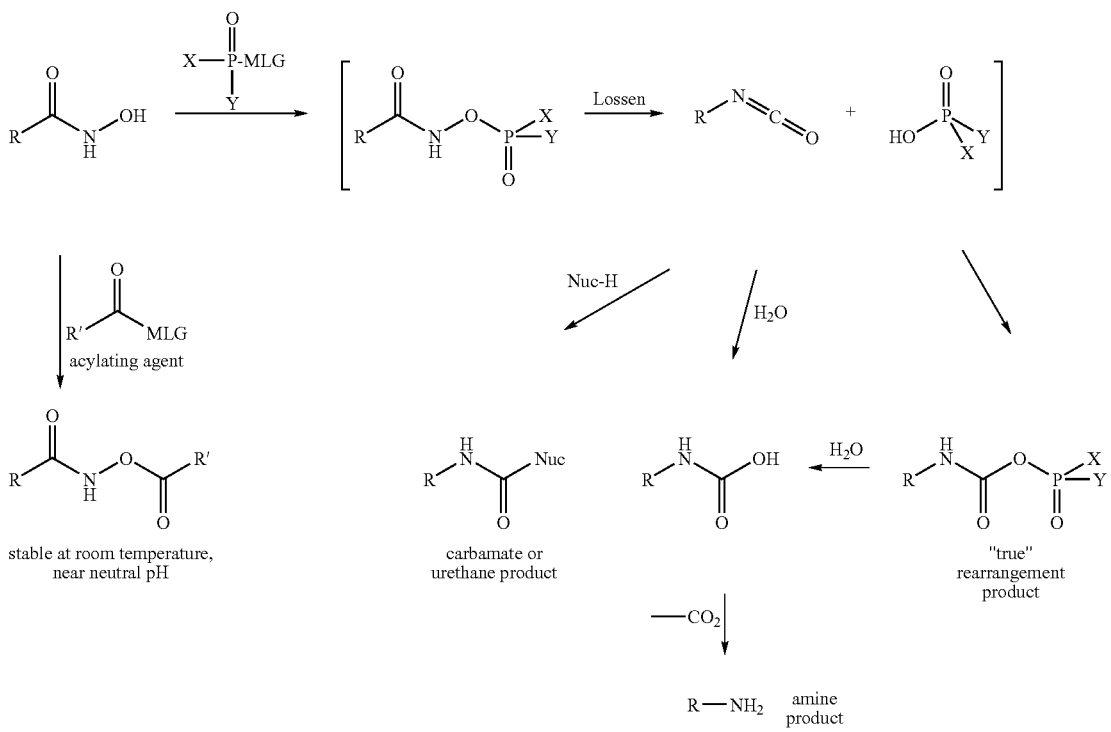

It is noteworthy that similar reaction with an acylating agent usually yields an adduct that is relatively stable; only upon treatment with base, or upon heating to high temperatures, or both, does rearrangement typically occur. Other compounds that will give the reaction-rearrangement sequence include sulfonyl halides and anhydrides. However, in the context of a nerve agent detection system that relies on the reaction-rearrangement sequence, sulfonyl halides and anhydrides would be unlikely to pose a problem. They are not effective nerve agents or vesicants, and are thus unlikely to be encountered in a battlefield or terrorist situation; furthermore, they are so reactive that they would likely react with atmospheric moisture before making it to a sensor system.

π-system (e.g., carotene, which is responsible for the orange color of carrots), it is much more commonly the case that dyes include aromatic rings (to give delocalized π-systems). For a given delocalized π-system, addition of polarizing groups (termed auxochromes) may significantly modify the dye characteristics. Incorporation of either electron donating groups or electron withdrawing groups will commonly lead to a moderate increase in $\lambda_{max}$ and $\epsilon$. However, it is most common to combine a donor at one end of the π-system with an acceptor at the other; this combination of donor and acceptor act synergistically to give a highly polarized π-system that exhibits dramatic increases in both $\lambda_{max}$ and $\epsilon$ relative to the unsubstituted compound.

Scheme 3: Beckmann and abnormal Beckmann reactions of oximes with phosphorus based nerve agents.

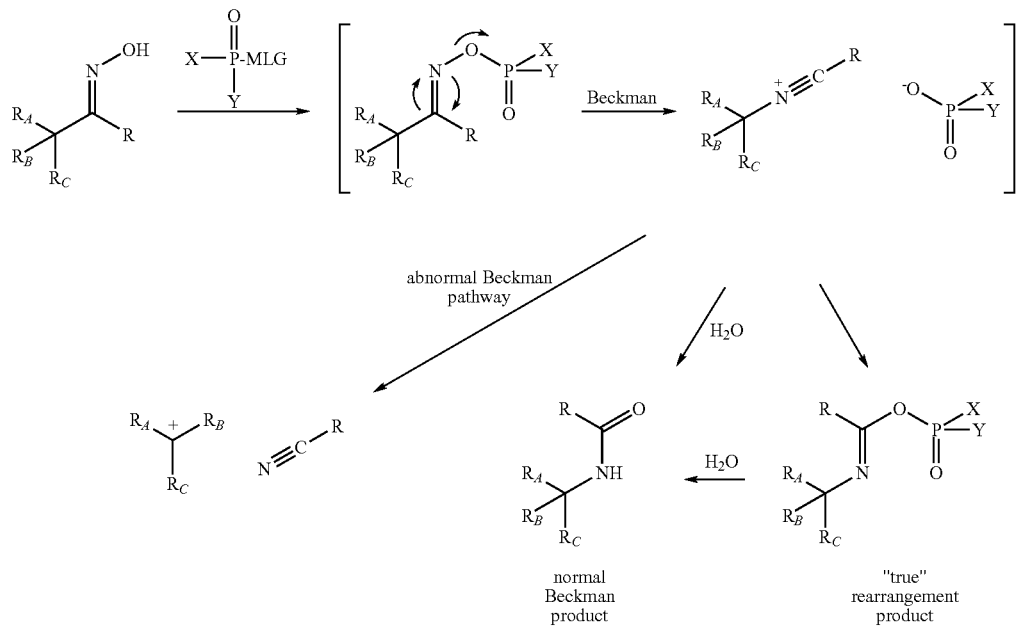

Oximes are a second class of hydroxylamine derivatives that, in certain circumstances, undergo a rearrangement reaction that can be useful in the detection of nerve agents Reaction of an oxime or its corresponding anion (an oximate) with a phosphorylating agent leads to what is termed a Beckmann rearrangement. Scheme 3 shows Beckmann and abnormal Beckmann reactions of oximes with phosphorus based nerve agents useful in the present methods. Though this reaction typically leads to amides, in cases in which the amide nitrogen would be attached to a carbon that could form a stable carbocation an abnormal Beckmann rearrangement occurs to give a nitrile and the corresponding carbocation, which can subsequently react with other nucleophiles (or not; see below). It is the abnormal Beckmann rearrangement that is of interest in the context of the $Sens_{conj}$ invention described below, while the normal Beckmann rearrangement may be of use in the $Sens_{mod}$ invention.

Characteristics of Dye molecules. Molecules behave as visible dyes because of the ready excitation of an electron from the ground state to an excited state upon adsorption of a photon of light (visible light in the case of dyes that act as such to the naked eye). Although a variety of compounds can act as dyes, a feature common to most is an extensive conjugated π-system—an uninterrupted series of p-orbitals that can be oriented so as to achieve overlap of the orbitals. While there are some compounds that only have a linear, conjugated Properly combined, the three features discussed above, (i) heightened reactivity of alpha-effect nucleophiles, (ii) rearrangement of adducts between certain alpha-effect nucleophiles, and (iii) dye characteristics, allow for an invention that allows for the rapid, specific and sensitive detection of nerve agents.

Nerve Agent Detection using Chemical Reaction-Rearrangement to Establish or Modify Dye Properties This aspect of the present invention comprises two broad strategies for nerve agent detection, each of which utilizes sensor molecules in a reaction-rearrangement sequence with the nerve agents. Importantly, this reaction rearrangement sequence results in the replacement of a carbon-carbon bond with a carbon-nitrogen bond, constituting an oxidation of one of the carbons. In one of these strategies ($Sens_{conj}$) the reaction/rearrangement sequence results in a carbon-nitrogen bond that undergoes spontaneous solvolysis to give a highly conjugated system that leads to the establishment of dye properties in a sensor molecule that had little or no dye character prior to exposure to the nerve agent. In the other strategy ($Sens_{mod}$) the reaction/rearrangement sequence leads to a substantial modification of the properties of a dye by replacing an electron withdrawing carbon by a nitrogen that is electron donating by resonance.

Nerve Agent Detection by the Sens$_{conj}$ Strategy

Though nerve agent detection can be accomplished according to the Sens$_{conj}$ strategy using either oximes or hydroxamic acids as reactive functional groups in a reaction-rearrangement sequence, the discussion that follows will focus on oximes. It will be oblivious to those skilled in the art that equivalent methods may be practiced using hydroxamic acids. In the oxime variant of the Sens$_{conj}$ strategy for nerve agent detection the sp$^2$ hybridized carbon of an oxime is connected directly to an "insulating carbon." Features of this insulating carbon are:

i) it is sp$^3$ hybridized.

ii) in addition to its direct connection to the oxime carbon, the insulating carbon is connected to at least one, but preferably two (or three) π-systems. Each connection to a π-system must be direct; that is, the insulating carbon must be directly attached to an atom having a p-orbital that is part of the π-system. At minimum, each said π-system must comprise two atoms that are doubly or triply bonded. Preferably, each said π-system constitutes a conjugated π-system in which there is an uninterrupted sequence of p-orbitals (typically numbering 3-30) which are capable of a geometrical orientation that allows substantial overlap of any adjacent pair of p-orbitals. The atoms involved in this conjugated π-system may all be carbon, or may be a combination of carbons, nitrogens, oxygens and sulfur. In many instances it will be desirable to have one or more of the said conjugated π-systems be, or include an aromatic molecule. In cases in which there are two or more π-systems attached to the insulating carbon it may often be desirable to have the two or more π-systems connected to each other, though this may not be necessary. In those cases in which the two or more π-systems are connected, this connection may be direct, or through one or more sp$^3$ hybridized atoms, or may be through one or more sp$^2$ hybridized atoms. In the latter instance, the sensor molecule will comprise a cyclic array of p-orbitals that fails to be a continuous cyclic array of p-orbitals only due to the presence of the insulating carbon, and the attachment of the insulting carbon to "two" π-systems will actually be two attachments of the insulating carbon to different sites on a single conjugated π-system. In any of the possible π-systems (conjugated or non-conjugated) discussed above, there may be substituents on the atoms forming the π-system, with these substituents chosen from halide, alkyl, alkoxy, aryl, aryloxy, thioalkyl, thioaryl, dialkylamino, diarylamino, arylalkylamino, and heteroaryl. Considerations as to the specific choice of the one or more π-system(s) is further discussed below.

iii) in addition to the oxime and the at least one π-system, the insulating carbon must be directly connected to either one or two (depending on the number of π-systems) additional groups that do not substantially decrease the stability of a carbocation to which they are directly attached. This group may include hydrogen and alkyl, but will preferably include aryl, heteroaryl, vinyl and propargyl. In some systems, these groups may include halide, alkoxy, aryloxy, substituted or unsubstituted amines and thioalkyl or thioaryl groups, with the caveat that such groups may suffer from some degree of instability through hydrolysis subsequent to the detecting reaction-rearrangement event. Such hydrolytic instability can be ameliorated in all but the halide substituents by further attachment of the oxygen, nitrogen or sulfur atoms to another portion of the sensor molecule. The specific identity of the additional group will be dependent in some degree on the number and nature of the π-systems attached to the insulating group, with a key factor in this decision being the stability of the carbocation that would be formed upon loss of the oxime group subsequent to the reaction-rearrangement sequence; formation of a more stable carbocation will generally be advantageous to the operation of the invention.

Operation of the Sens$_{conj}$ Invention

Two embodiments of the Sens$_{conj}$ invention are illustrated in Scheme 4, which illustrates operation of two preferred embodiments of the Sens$_{conj}$ invention wherein the group undergoing the reaction-rearrangement sequence is a hydroxamic acid. Reaction of compositions 1 or 2 with a nerve agent XYP(O)MLG leads, through a spontaneous abnormal Beckmann rearrangement, to the dyes pyroninY and rhodamine B, respectively. Thus, reaction of 1 with a nerve agent or nerve agent simulant will lead to transient formation of adduct 1a, which will then undergo spontaneous Beckmann rearrangement to give the N-alkylated nitrile 1b. Under suitable conditions, this N-alkylated nitrile will undergo solvolysis to give the known dye pyronin, 1c. Similarly, compound 2 will react with a nerve agent or nerve agent simulant to provide the known dye rhodamine B.

Scheme 4: Operation of two preferred embodiments of the Sens$_{conj.}$ invention that utilize oximes for the detection event.

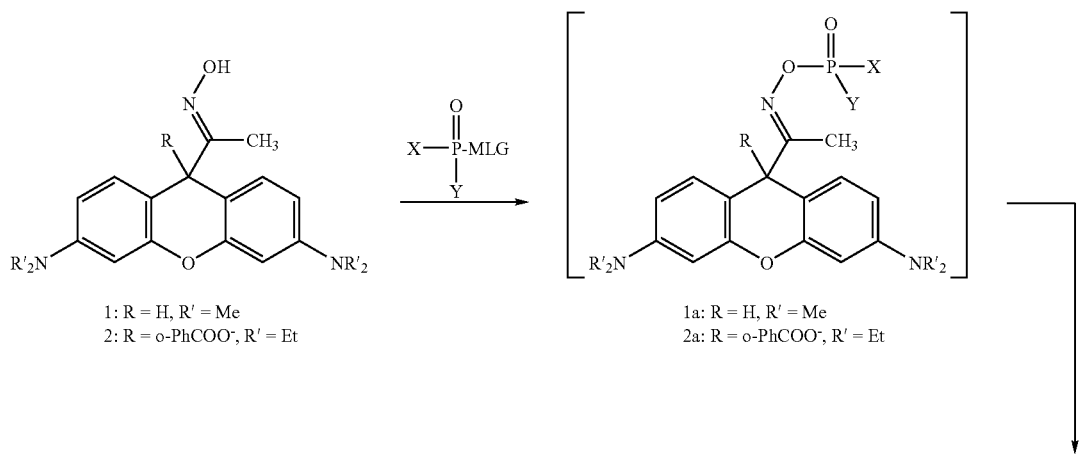

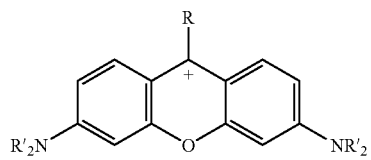

1c: R = H, R' = Me (pyronin Y, $\lambda_{max}$ 548 nm)
2c: R = o-PhCOO⁻, R' = Et (rhodamine B, $\lambda_{max}$ 543 nm)

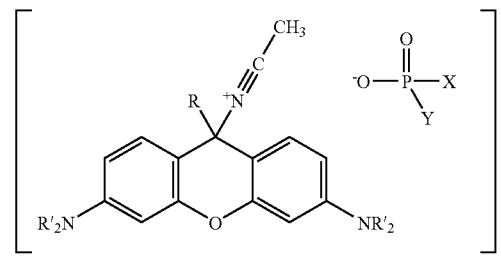

1b: R = H, R' = Me
2b: R = o-PhCOO⁻, R' = Et

As illustrated in Scheme 5, compounds 1' and 2' are analogous to compounds 1 and 2, but incorporate hydroxamic acids instead of the oximes of the latter two compounds. In a pair of embodiments closely related to those described above for compositions 1 and 2, reaction of compositions 1' or 2' with a nerve agent XYP(O)MLG leads, through a spontaneous Lossen rearrangement, to the dyes pyronin Y and rhodamine B, respectively. As is specifically illustrated herein, compound 1' is particularly attractive because of its ready synthesis from commercially available pyronin Y. Reaction of 1' with a nerve agent or nerve agent simulant will lead to transient formation of adduct 1a', which will then undergo spontaneous Lossen rearrangement to give the isocyanate 1b'. Under suitable conditions, this isocyanate will undergo solvolysis (either directly, or by way of the corresponding carbamic acid) to give the known dye pyronin, 1c. Similarly, compound 2' will react with a nerve agent or nerve agent simulant to provide the known dye rhodamine B.

In all of the described embodiments 1/1' and 2/2' it may be preferential to utilize the conjugate base of the oxime or hydroxamic acid (i.e., the oximate or hydroxamate), due to the greater nucleophilicity of the basic forms. Alternatively, a base may be incorporated in the reaction medium (the matrix) or as a part of the sensor molecule to serve as a general base catalyst for the reaction. Replacement of the dialkylamino groups of 1/1' and 2/2' with hydroxyl groups would also provide effective Sens$_{conj}$ compounds (e.g., such a replacement in 2 or 2' would give the known dye fluorescein), as would partial replacement (to give mixed hydroxy/amino compounds), or the use of mono-alkylamino or simple amino groups in place of the dialkylamines. It is also obvious to one skilled in the art that the R group of 1/1' or 2/2' could be replaced in some instances with an alkyl group, or more beneficially with alternative aryl groups, alkenyl (or polyalkenyl), or alkynyl (or polyalknyl) groups. Addition of additional substituents to the basic xanthene ring systems of 1/1'

Scheme 5: Operation of two preferred embodiments of the Sens$_{conj}$ invention that utilize hydroxamic acids for the detection event.

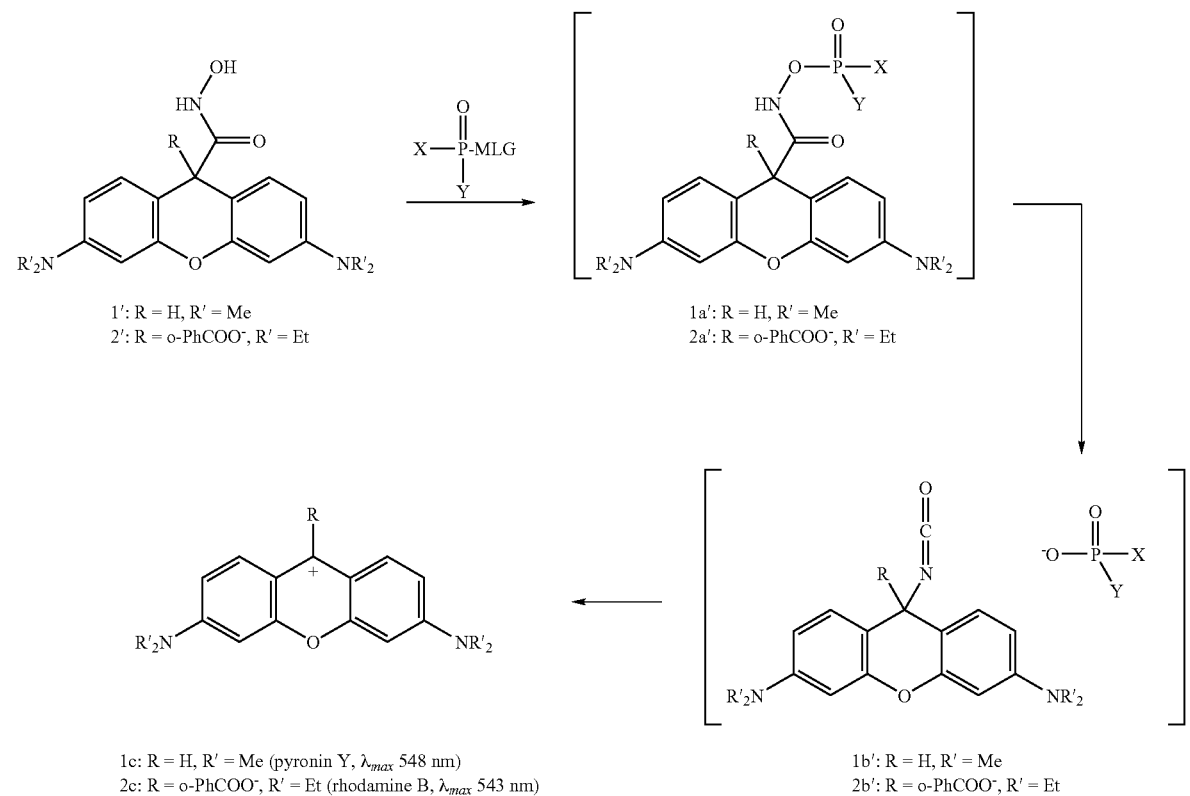

1': R = H, R' = Me
2': R = o-PhCOO⁻, R' = Et

1a': R = H, R' = Me
2a': R = o-PhCOO⁻, R' = Et

1c: R = H, R' = Me (pyronin Y, $\lambda_{max}$ 548 nm)
2c: R = o-PhCOO⁻, R' = Et (rhodamine B, $\lambda_{max}$ 543 nm)

1b': R = H, R' = Me
2b': R = o-PhCOO⁻, R' = Et and 2/2' would also provide compounds that would function in a fashion similar to these compounds.

Specificity for Nerve Agents

The issue of specificity has largely been discussed above, and is inherent to the reaction-rearrangement sequence that is a part of the invention. Relatively few compounds will react with the oxime (or oximate), and of those that will, even fewer will subsequently undergo an abnormal Beckmann reaction. However, a further element of specificity is obtained by measuring the rate of color formation. Very slow color formation will be more characteristic of nerve agent analogs (e.g., insecticides) that, while toxic under conditions of long term exposure, are not of the immediate concern represented by actual chemical warfare agents. Conversely, very unusually high rates of color change (relative to those seen with nerve agents) is characteristic of nerve agent analogs possessing good leaving groups (e.g., chloride, bromide, iodide). Though undesirable due to vesicant-like characteristics (formation of mineral acids on exposure to water), these compounds will not be as toxic as nerve agents due to their ready hydrolysis in the body.

Detection of the Reaction-Rearrangement Sequence

In one embodiment, detection of the reaction-rearrangement sequence (and thus, by inference, the nerve agent) may be accomplished either visually or through the use of instrumental methods, such as spectroscopic analysis. One of the great advantages of the $Sens_{conj}$ method over other means of nerve agent detection is that the starting sensor compounds are uncolored or very slightly (e.g. very light yellow) colored, whereas the product resulting from exposure to the nerve agent and the subsequent reaction-rearrangement sequence is a dye, and strongly colored. Visual detection, by development of a new color in an otherwise slightly colored, or colorless sample matrix is obviously the most convenient and inexpensive method; it would be useful for protecting individuals, or for inexpensive test kits used by local fire departments or law enforcement agencies (who will often operate with protective equipment). However, given the high toxicity of nerve agents, it will often be desirable to detect nerve agents at a remote site, or at a concentration so low that a visible color reaction would not be evident. Instrumental methods will most commonly include UV-Visible spectroscopy, fluorescence spectroscopy, infrared spectroscopy and Raman spectroscopy (both conventional and surface enhanced Raman scattering (SERS) spectroscopy). While any of these methods should be satisfactory to some degree, the particular requirements of the situation will often dictate which method is used. UV-Visible spectroscopy is particularly suitable for situations in which a low cost detection system is desirable. Higher sensitivities (at a higher price) will be obtainable using fluorescence, infrared and SERS methods. It is also the case that the structure of the sensor molecule will influence the spectroscopic method chosen. For example, compound 2c (Rhodamine B) of scheme 4 is a well known fluorescent dye, as is the analogous compound in which the diethylamino groups of compound 2c of scheme 4 are replaced by hydroxyl groups (fluorescein); these compounds would be particularly well suited for fluorescence detection, though UV-Vis and Raman methods could also be used. On the other hand, there are many dyes that do not show significant fluorescence (e.g., see compound 3 of Scheme 6), and detection of such compounds may be best accomplished using UV-Vis and Raman methods.

The Sample Matrix for the $Sens_{conj}$ Compound

The $Sens_{conj}$ compound may be in solution, may be adsorbed/deposited on a solid or particle, or may be attached in some way to a polymer. For example, detection systems that rely on visual detection may have $Sens_{conj}$ compounds adsorbed onto paper or other cellulosic or fibrous materials, or may have them attached to a polymer by way of ionic bonds or covalent bonds. Ionic attachment may be accomplished by incorporating one or more cationic/anionic group(s) into the structure of the $Sens_{conj}$ compound and ion pairing that with anionic/cationic group(s) on a polymer (e.g., an ion exchange resin). Incorporation of cationic/anionic group(s) in the $Sens_{conj}$ skeleton should be straightforward. For example, in compounds 1 or 2 of Scheme 4 or 1' or 2' of Scheme 5 the methyl/ethyl groups could be replaced by alkyl or aryl chains bearing the appropriate charged group(s). Alternatively, one of the hydrogens of the ring, or the R group could be replaced by a group having a charged moiety. In a similar fashion, R and/or R' or H's of the rings of compounds 1 or 2 of Scheme 4 or 1' or 2' of Scheme 5 may be replaced by alkyl or ether chains that would, in turn, be attached by covalent bonds to a polymer. Alternatively, instead of attachment to a polymer, alkyl or ether chains could be terminated with groups having a high affinity for silver, gold or copper (e.g., thiols, thioethers, nitrogen heterocycles, polyanionic groups) to provide for attachment to silver, gold or copper surfaces or colloids or other nanoparticles to allow for the use of SERS.

Other Dye Precursors for the $Sens_{conj}$ Variant of the Invention

Upon exposure to nerve agents, the examples of $Sens_{conj}$ compounds given above (compounds 1 and 2 in Scheme 4 or 1' or 2' of Scheme 5) are converted to xanthene dyes; however, it may be desirable in some cases to have other dyes be produced as a result of the reaction-rearrangement sequence. Reasons for having other dyes formed my include cost of synthesis, ease of synthesis, stability under the conditions in which the detection system is to be employed, color and/or spectral characteristics, and suitability to a particular spectroscopic detection method (e.g., a highly fluorescent dye may be undesirable for a Raman based detection method due to the high background produced). Changes to compounds 1 and 2 of scheme 4 or 1' or 2' of Scheme 5 included in the present invention include replacement of the oxygen atom by sulfur, selenium, nitrogen (or substituted nitrogen), phosphorus (or substituted phosphorus) or arsenic (or substituted arsenic).

More substantial changes to the dye structure are also possible, as will be briefly outlined below. In the discussion that follows, it is obvious that the same considerations discussed above with regard to specificity, detection method and sample matrix apply to other dye classes; thus, these considerations will not be explicitly considered for each example of a dye. Furthermore, it should be understood that the examples given below may not constitute an exhaustive list of compounds suitable for the purpose of the $Sens_{conj}$ invention, but simply serve as illustrations of the above-described principles of the operation of this invention.

Di- and triarylmethane $Sens_{conj}$ Sensor Compounds

In the examples given above, compounds 1 and 2 of Scheme 4 or 1' or 2' of Scheme 5, the insulating carbon bearing the oxime or hydroxamic acid is attached directly to two atoms having p-orbitals that are, in turn, connected through a series of atoms, each of which have p-orbitals overlapping with neighboring atoms; thus, the insulating atom is attached to two points of a single π-system. As noted in the general description of the invention, it is also possible for the insulating atom to be attached to two isolated π-systems. Scheme 6 illustrates example embodiments of the $Sens_{conj}$ invention in which tri- and diarylmethane dyes are formed in which exposure of sensor compounds 3, 4, 5, or 6 leads to formation of what are commonly termed tri- and diarylmethane dyes. Thus, reaction of virtually colorless compound 3 (or its conjugate base) with a nerve agent XYP(O)MLG leads to formation of the phosphorylated oxime 3a, which will rearrange to the N-alkylated nitrilium 3b, which will then fragment to 3c. Compound 3c is the triarylmethane dye Malachite Green, having a $\lambda_{max}$ of 615 nm, and this change in color will be readily observed either by visual (for relatively high concentrations of nerve agent) or instrumental methods, as discussed above. Similarly, reaction of a nerve agent with essentially colorless compound 4 (or its conjugate base salt), in which the dimethylamine donor groups of 3 have been replaced by oxygens, will lead to an abnormal Beckmann reaction that produces the sulfophthalein dye Phenol Red.

these compounds that might lead to desirable physical properties (e.g., with respect to adsorption to a support, or stability towards air or water).

In all of the examples of $Sens_{conj}$ sensor compounds given above, the insulating atom bearing the oxime (or oximate) group is directly attached to aromatic rings that are either isolated from one another (as in compounds 3-6 of Scheme 6), or connected in some way (as in compounds 1 and 2 of Scheme 4 or 1' or 2' of Scheme 5). It is clear from the general discussion of "Nerve Agent Detection by the $Sens_{conj}$ Strategy" above that direct attachment of the insulating atom to one or more aromatic rings is not necessary. For example, replacement of the R group in compounds 1, 1' and 3 with a Scheme 6. Operation of the $Sens_{conj}$ invention in which tri- and diarylmethane dyes are formed.

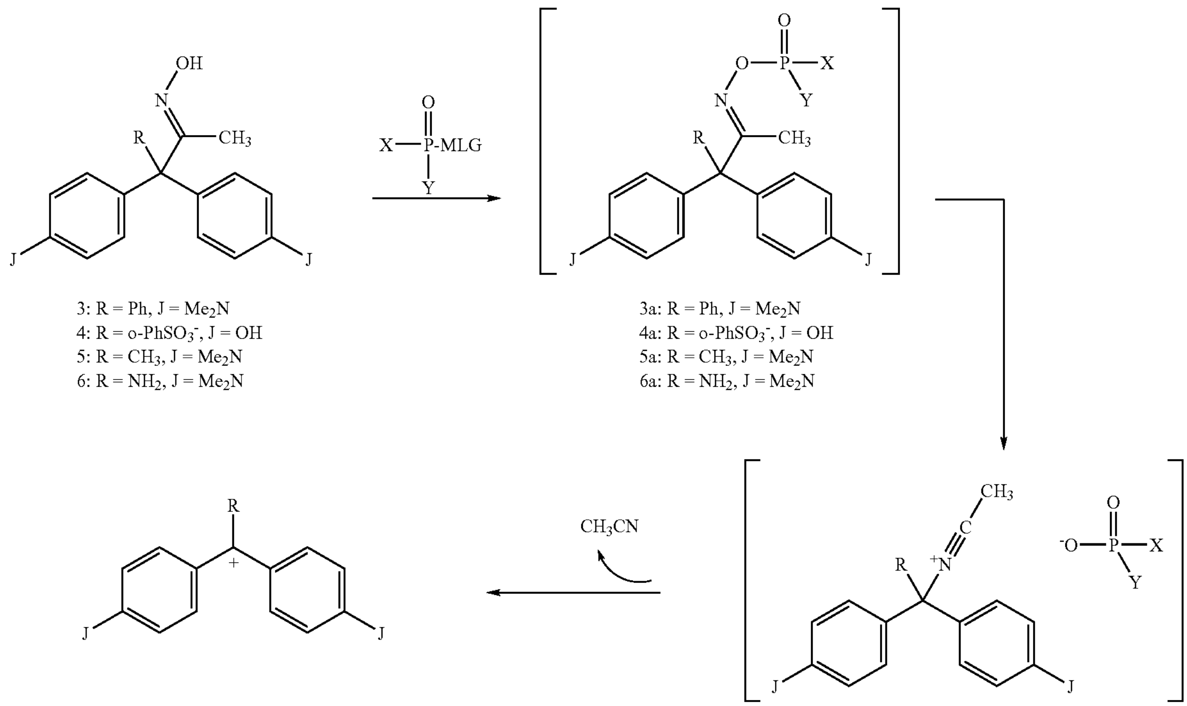

3: R = Ph, J = $Me_2N$
4: R = o-$PhSO_3^-$, J = OH
5: R = $CH_3$, J = $Me_2N$
6: R = $NH_2$, J = $Me_2N$

3a: R = Ph, J = $Me_2N$
4a: R = o-$PhSO_3^-$, J = OH
5a: R = $CH_3$, J = $Me_2N$
6a: R = $NH_2$, J = $Me_2N$

3c: R = Ph, J = $Me_2N$ (Malachite Green, $\lambda_{max}$ 615 nm)
4c: R = o-$PhSO_3^-$, J = OH/$O^-$ (Phenol Red, $\lambda_{max}$ 557 nm)
5c: R = $CH_3$, J = $Me_2N$ ($\lambda_{max}$ 600 nm)
6c: R = $NH_2$, J = $Me_2N$ (Auramine O, $\lambda_{max}$ 432 nm)

3b: R = Ph, J = $Me_2N$
4b: R = o-$PhSO_3^-$, J = OH
5b: R = $CH_3$, J = $Me_2N$
6b: R = $NH_2$, J = $Me_2N$

It is not necessary to have triarylmethanes result from the reaction-rearrangement sequence; two examples of the formation of diarylmethane dyes are also illustrated in Scheme 6 for sensor compounds 5 and 6, in which dyes having $\lambda_{max}$ values of 600 nm and 432 nm, respectively, are produced. These compounds illustrate the fact that the third aryl group found in compounds 3 and 4 in Scheme 6 can be replaced by either alkyl (as in compound 5) or heteroatom (as in compound 6) groups. It will be clear to one of skill in the art that the same considerations discussed for compounds 1 and 2 of Scheme 4 or 1' or 2' of Scheme 5 with respect to specificity, methods of detection, and the sample matrices in which the $Sens_{conj}$ compounds are presented apply to compounds 3, 4, 5 and 6 of Scheme 6. Furthermore, that—as is the case for compounds 1 and 2 of Scheme 4 or 1' or 2' of Scheme 5—it may be desirable to introduce additional substituents into 4-dimethylaminophenylacetylene group, 4-$(CH_3)_2NPhCC$—, leads to dyes that have their principle absorbance bands in the near infrared (Akiyama et al. *Chemistry Letters* 1981 p. 311 and Akiyama et al. *J. Chem. Soc. Chem. Commun.* 1987 p. 710). Indeed, there is no necessity that an aromatic ring be involved at all in the $Sens_{conj}$ sensor compound. Scheme 7 shows an embodiment of the present invention wherein the natural dye β-carotene is formed upon a reaction-rearrangement sequence involving compound 7 with a nerve agent. Exposure of compound 7 will lead to initial reaction to 7a, followed by Beckmann rearrangement to 7b and fragmentation to 7c, which will lose a proton to provide the orange β-carotene. This is illustrated in Scheme 7 for compound 7, which forms the natural dye β-carotene upon the reaction-rearrangement sequence with a nerve agent. This example is chosen for convenience, and because the dye formed is a known compound; it will be obvious to one skilled in the art that the position of the insulating atom in the carbon chain could be varied. Furthermore, spectral characteristics (e.g., color) of the dye resulting from the reaction-rearrangement sequence may be varied in a predictable fashion on the basis of Woodward's rules for conjugated alkenes. Thus, changing the number of carbon-carbon double bonds that are present will lead to substantial changes in $\lambda_{max}$ in the final dye, while changing the number and type of substituents on the carbon chain will lead to more subtle changes in $\lambda_{max}$. This example is also noteworthy in that the final dye formed is not a cationic dye, but a neutral compound.

Other Oxime and Hydroxamic Acid Variants of the $Sens_{conj}$ Invention

In many examples of the $Sens_{conj}$ invention given above, the insulating carbon is attached to a methyl oxime; i.e., the compounds are of the form RR'{insulating carbon}C(CH$_3$)=NOH. It should be obvious to one skilled in the art that the methyl group could be replaced by other alkyl groups than methyl, providing that such group does not preferentially lead to an alternative Beckmann rearrangement. It may also be advantageous to use a substituted alkyl group (e.g., trifluoromethyl) that would increase the acidity of the oxime, thereby making it easier to form the oximate.

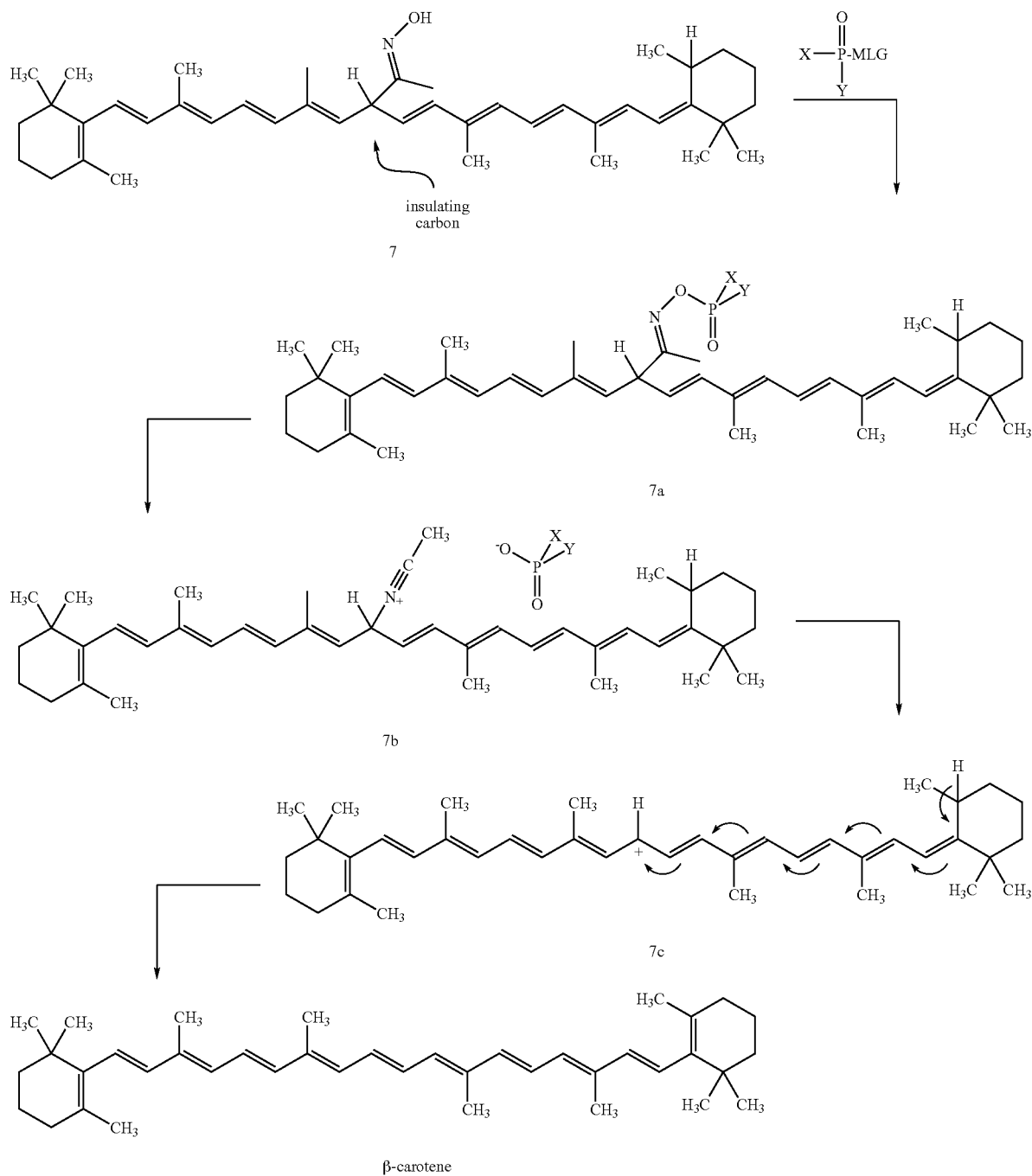

Scheme 7. An embodiment of the present invention wherein the natural dye β-carotene is formed upon a reaction-rearrangement sequence.

Though the use of oximes/oximates in the $Sens_{conj}$ invention has the desirable feature that the resulting rearrangement reaction leads to an N-alkylated nitrilium ion that will be particularly prone to fragmentation to a nitrile and carbocation, there are instances in which use of a hydroxamic acid is preferred. Examples of this substitution of oxime by hydroxamic acid were given in Scheme 5, above, and similar substitutions could be made for compounds 3-7. As discussed above, hydroxamic acids spontaneously undergo a Lossen rearrangement upon reaction with nerve agents, leading to an intermediate isocyanate (See, e.g., Scheme 2). If a hydroxamic acid is attached to an insulating carbon having the characteristics outlined above in the beginning of the "Nerve Agent Detection by the $Sens_{conj}$ Strategy" then the isocyante may spontaneously solvolyze to give HN═C═O (which will undergo subsequent solvolysis by water) and the same carbocation dye that would result from the reaction-rearrangement sequence described for the oxime-based sensor molecules. Alternatively, the intermediate isocyanate may react with other nucleophiles (See, e.g. Scheme 2) and these products may subsequently solvolyze to give the detectable dye carbocation.

There may be both advantages and disadvantages associated with use of a hydroxamic acid in place of an oxime in the $Sens_{conj}$ invention. Hydroxamic acids are more acidic than oximes, and the resulting hydroxamate is more nucleophilic; thus, it will usually be the case that hydroxamic acids/hydroxamates will be superior (e.g., in terms of rate of reaction) to oximes in their reactions with nerve agents. For example, the reaction of benzhydroxamic acid with diisopropylfluorophosphate is quite rapid even at pH levels that are only slightly basic (ca. 7.8). On the other hand, the rate of solvolysis of the isocyanate (or its reaction products) is generally expected to slower/more difficult than that of the nitrile of the N-alkylated nitrilium formed in the abnormal Beckmann reaction of oximes. Thus, in those cases in which it is considered preferable to employ a hydroxamic acid in place of an oxime in the $Sens_{conj}$ invention it will be desirable to use sensor molecules in which the insulating atom will be transformed to a particularly well stabilized carbocation, thereby facilitating the solvolytic dye-forming reaction.

Nerve Agent Detection by the $Sens_{mod}$ Strategy

As discussed above, the basis of the $Sens_{conj}$ nerve agent detection method is the formation of a dye from a non-dye compound in a manner that is dependent on a nerve agent initiated reaction-rearrangement sequence that establishes a larger, or more highly conjugated π-system. The basis of the $Sens_{mod}$ detection method is the modification of the spectroscopic characteristics of an existing π-system through a nerve agent initiated reaction-rearrangement that replaces an electron withdrawing carbon in a carbon-carbon bond with an electron donating nitrogen in a carbon-nitrogen bond. This modification of the spectroscopic characteristics of an existing π-system is accomplished by changing an electron withdrawing hydroxamic acid or oxime group into an electron donating amine/carbamate or amide group, respectively. The essential features of this invention are a conjugated π-system and a hydroxamic acid (or oxime) directly attached to it, such that the carbon of the hydroxamic acid (or oxime) is conjugated with the π-system. In the preferred embodiments of the invention the conjugated π-system to which the hydroxamic acid (or oxime) is conjugated will have a substantial peak (ϵ>1,000 with much larger values preferred, e.g. >20,000) with an absorption in the electronic spectrum (UV-Vis-NIR) between 350 and 1200 nm, and preferentially between 450 and 1100 nm. The specifically preferred absorbance maximum will depend on the structure of the dye and the method of detection employed (see below).

Operation of a Preferred Embodiment of the $Sens_{mod}$ Invention

In most cases it will be preferable to employ hydroxamic acids, instead of oximes, in the $Sens_{mod}$ nerve agent detection invention; as discussed above, the hydroxamic acids typically have superior characteristics with respect to their reactivity with nerve agents and rates of the subsequent rearrangement reaction (e.g., reaction and rearrangement is rapid even at pH 7.5-8, and even faster at higher pH values, due to a greater concentration of the highly reactive hydroxamate). Thus, the discussion that follows will focus on the use of hydroxamic acids. However, it may be the case that for reasons of ease of synthesis, cost of synthesis, particular reactivity or physical properties, or other reasons it may be preferable to employ oximes instead of hydroxamic acids.

Several variants of a preferred embodiment of the $Sens_{mod}$ invention are illustrated in Scheme 8 (sensor compounds 8, 9, 10 and 11). The operation of the invention will be discussed in detail for compound 8. However, the essential features of the operation of the remaining compounds are the same, involving the modification of the properties of an azo dye as a result of a reaction-rearrangement sequence; the differences between the compounds and each other primarily have to do with sample matrix and detection characteristics.

Scheme 8: Several variants of the $Sens_{mod}$ invention based on modification of the spectral properties of azo dyes.

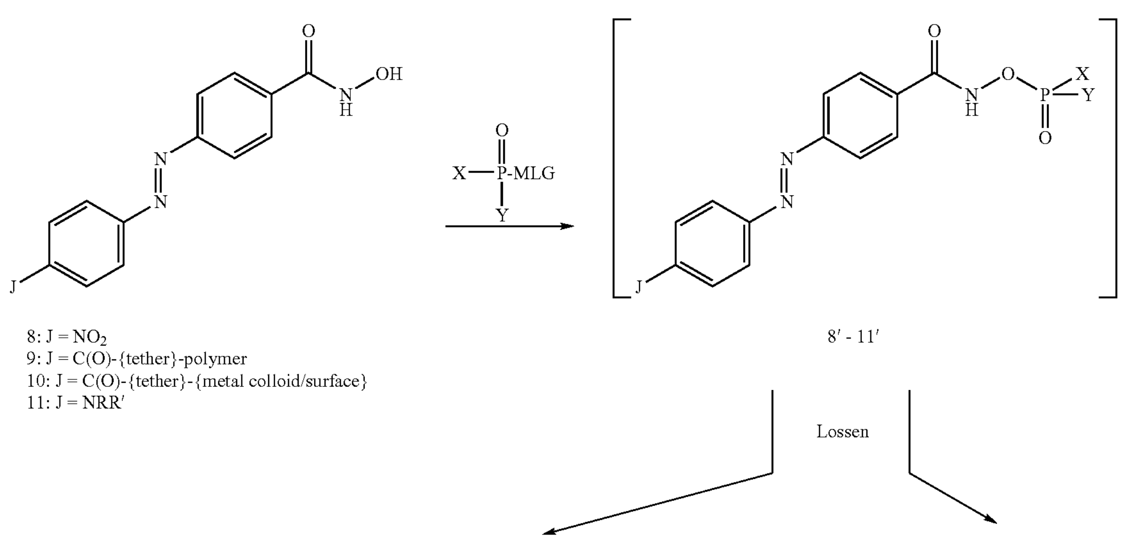

8: J = $NO_2$
9: J = C(O)-{tether}-polymer
10: J = C(O)-{tether}-{metal colloid/surface}
11: J = NRR′

8′ - 11′

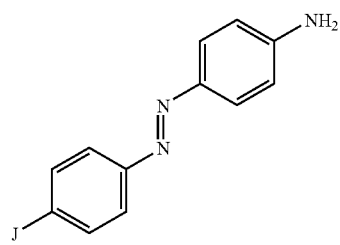
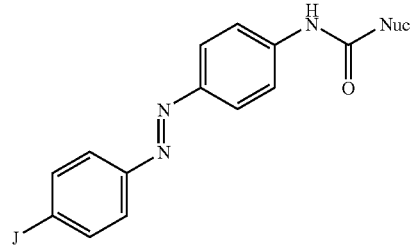

8b: J = NO₂
9b: J = C(O)-{tether}-polymer
10b: J = C(O)-{tether}-{metal colloid/surface}
11b: J = NRR'

8a: J = NO₂
9a: J = C(O)-{tether}-polymer
10a: J = C(O)-{tether}-{metal colloid/surface}
11a: J = NRR'

Compound 8 of Scheme 8 is a dye with a relatively low value of $\lambda_{max}$, due to the fact that the diphenylazo chromophore is terminated at each end by electron withdrawing groups (Hammett $\sigma_p$ of NO₂ is 0.81, while $\sigma_p$ of C(O)NHOH is ~0.4 as used herein $\sigma_p$ refers to Hammett $\sigma_p$ unless otherwise noted). Reaction of 8 with a nerve agent XYP(O)MLG will lead to 8', which will undergo Lossen rearrangement to give 8a and 8b. Absent any added nucleophiles (e.g., other than water, which leads to 8b), the likely identity of the nucleophile in 8a is another hydroxamic acid molecule, and the relative proportions of 8a and 8b will be concentration dependent; lower concentrations will favor 8b. Regardless of the proportions of the two products, a marked change in the spectral properties will result, due to the dramatic change in the donor-acceptor properties consequent upon changing the —C(O)NHOH group ($\sigma_p$~0.4) to a carbamate —NHC(O)OR ($\sigma_p$~0.15) or an amino group ($\sigma_p$~0.30). Thus, while the substituents (nitro and hydroxamic acid) in compound 8 have only a small net difference in $\sigma_p$ values (of 0.41), the difference in the products (nitro vs. carbamate or amino) are 0.96 and 1.11 for compounds 8a and 8b, respectively. This change in spectral characteristics should be visually detectable, since the moderately colored compound 8 will change, in part, to the known dye Disperse Orange 3 (8b of Scheme 8).

Compound 8 of Scheme 8 illustrates one of the simplest, but effective embodiments of the $Sens_{mod}$ invention, in that it constitutes a hydroxamic acid group directly attached to an existing chromophore which undergoes a substantial change in its spectral characteristics upon a nerve agent initiated reaction-rearrangement sequence. The remainder of the examples illustrate modifications of this simple embodiment that may provide superior performance of the invention in certain circumstances.

Attachment of the $Sens_{mod}$ Device to Polymers

Compound 9 (See, Scheme 8) constitutes an embodiment of the $Sens_{mod}$ invention in which the detecting portion of the sensor molecule (i.e., the hydroxamic acid-chromophore system) is attached by way of a tethering subunit to a polymer. If the length of this tethering subunit is appropriately short there will be no possibility that two of the hydroxamic acid portions of the sensor molecule subunits can interact. The effect of this separation of the detecting portions of the sensor molecules will generally be to greatly enhance, possibly to the point of exclusivity, the formation of compound 9b, since compound 9a will most commonly represent the product of the reaction of the intermediate isocyanate and a second hydroxamic acid (See, e.g. Scheme 3); if the detecting portions are sufficiently separated, this reaction cannot occur. This will result in an increase in detection sensitivity since those detector molecules that would otherwise be "wasted" in reaction with isocyanates will still be available for reaction with nerve agent. Of likely greater importance, the fact that a greater proportion of (or exclusive) formation of compound 9b will mean that the overall change in spectral characteristics will be greater, since the $\sigma_p$ value of the amine of compound 9b is more negative than that of compound 9a. A further advantage of this embodiment of the invention of particular relevance to instrumental detection of the reaction-rearrangement sequence is that signals associated with the process will be more intense, since they will not be lessened by the formation of multiple products (e.g., if the process produces two compounds in equal amounts, then the signal intensities of peaks unique to the two compounds will be half the intensity they would be if they were produced as the only products).

There are a number of features of note about this polymeric version of the $Sens_{mod}$ invention:

a) Detection methods. Visual detection may still be effective using this variant of the $Sens_{mod}$ invention. Raman spectroscopy will also be effective, since it involves scattered radiation. If the polymer is further treated with silver or gold in some way (e.g., with colloids) it may be that signal enhancement will result due to the SERS effect. Fluorescence spectroscopy would be unlikely to be effective with the particular example chosen (azo dyes are not typically fluorescent), but polymer bound variants of the $Sens_{mod}$ invention that produce fluorescent molecules (see below) should be well suited for detection by this method. Provided that the polymer to which the detecting subunit (hydroxamic acid with conjugated π-system) forms a substantially clear film or glass, then spectroscopic methods such as UV-Vis or infrared will be suitable for detection of the reaction-rearrangement sequence.

b) The Tethering Group. The detection portion of the sensor molecule is attached to the polymer by a tethering group that is sufficiently short that interaction between the hydroxamic acid portions of the molecules is not possible. Though this interaction will also depend upon the degree of loading onto the polymer, preferred tether lengths will be 1-6 atoms, though longer chains (to 50 atoms) may sometimes be appropriate. The tethering group will most commonly be alkyl or substituted alkyl, aryl or substituted aryl, but these chains may also include heteroatoms such as oxygen (e.g., ethylene and polyethylene glycols, propylene and polypropylene glycols, etc.), sulfur, selenium, nitrogen and phosphorus. In compound 9 the tether is attached to a carbonyl carbon. This mode of attachment would be particularly convenient if the tether precursor was an amino terminated chain, since this would constitute an amide linkage, which is readily formed synthetically. It should be stressed, however, that the tether does not need to be attached in this position, or to a carbonyl group; the tether could be attached to any of the positions on either of the aromatic rings making up the dye, or through some linkage to another substituent on the dye.

c) The polymer, or other solid support. There are few restrictions relating to the polymer to which the detection portion of the sensor molecule is connected. From a practical standpoint, commercially available polymers having reactive groups capable of being chemically linked to a tethering group will be preferred. These include polymers having pendant epoxide, carboxylic acid, carboxylic acid anhydride, amine, isocyanate, isothiocyanate, and other reactive groups. It is also possible to affix sensor molecules to a solid support through non-covalent bonds. For example, a sensor molecule having a tethering group that is terminated in an ammonium or quaternary ammonium ion could be loaded onto a strong or weak cation exchange resin (e.g., a benzenesulfonate or benzoate, respectively); provided that the resulting detection device was not exposed to ion containing liquids (e.g., salt solutions) the sensor molecules would be as effectively immobilized as if they were covalently attached. Similarly, a tethering group terminated by an anionic group such as a sulfonate, sulfate ester, phosphate/phosphate ester, phosphonate/phosphonate ester or carboxylate could be ion paired with the positively charged groups of an anion exchange resin (e.g., benzyltrimethylammonium or pyridinium resin). Immobilization could also be accomplished through absorption to a simple cellulosic solid support, such as filter paper. In such systems it may be desirable to introduce additional groups onto the sensor molecule that inhibit mobility (these groups could be highly polar or highly non-polar, depending on the filter medium).

Attachment of the Sens$_{mod}$ Device to Metal Surfaces

Compound 10 in Scheme 8 illustrates a variant of the invention in which the detection portion of the molecule is attached by way of a tether to a metal surface. The metals of choice for this application will typically be silver, gold and copper, with the former two being most preferred for some applications. The metal surface may be a conventional metal surface (e.g., a foil), or a metal colloid, or a particle or surface of some other material (metal or non-metal) upon which silver, gold or copper has been deposited. The motivation for use of these variants of the Sens$_{mod}$ invention is that they will provide for sensitive detection when used with Raman spectroscopy; localization of the detection portion of the sensor near the silver, gold or copper surface will give rise to the SERS effect, with an associated high signal intensity. Because of the possibility of achieving greater signal intensity and therefore lower detection limits through surface enhanced resonance Raman scattering, it will usually be desirable in these inventions to utilize a conjugated π-system that provides, after the nerve agent initiated reaction-rearrangement sequence, a dye having its $\lambda_{max}$ at, or near the wavelength of the laser used in the Raman system being utilized for detection. Though this discussion has focused on the use of Raman spectroscopy, it is obvious to one skilled in the art that other means of detection could be used in such systems, including but not limited to fluorescence spectroscopy and reflectance infrared spectroscopy.

The same considerations discussed above for compound 9 (See, Scheme 8) apply to the makeup of the tethering group and its position and mode of attachment to the detection portion of the sensor molecule. However, in most instances the end of the tether being attached to the metal, colloidal metal or metal nanoparticle surface will have a thiol or phosphine, though polar groups including mono-, di- or polycarboxylates, sulfates, sulfonates, phosphates, phosphonates, ammoniums, or nitrogen or sulfur heterocyclic compounds may also be effective for this purpose. A variant of this strategy is to combine the sensor molecule lacking the metal surface with a nerve agent, and then combine the resultant product with a metal surface, such as a foil, plate or colloidal or nanoparticle metal surface.

Sens$_{mod}$ Variants in Which a Dye-like Sensor becomes Less Dye-like

In most instances it will be the case that it is preferable to have a nerve agent initiated reaction-rearrangement sequence result in a product that is more dye-like than the starting sensor molecule (the product will have a higher $\lambda_{max}$, and/or higher $\epsilon$ than the starting sensor); as will have been gathered from the preceding discussions, this is readily accomplished by utilizing a sensor molecule having a hydroxamic acid and some other strong electron withdrawing group (e.g., nitro, sulfonate, phosphonate, arsenate, nitrile, ester, amide, ketone, aldehyde) on the other terminus of the conjugated π-system. However, it may also sometimes be desirable to have the detection event be a decrease in dye-like character. Though such systems could be used with visual detection (i.e., the fading of a color), they will most commonly be used in conjunction with spectroscopic detection devices. An example of a decrease in dye-like character is illustrated by compound 11 of Scheme 8. The starting sensor compound 11 will show good dye properties, since the electron withdrawing hydroxamic acid ($\sigma_p$~0.4) is paired with a strongly electron donating dialkylamino group ($\sigma_p$~-0.5), giving a $\sigma_p$ of ~0.9. Upon exposure to a nerve agent and the subsequent reaction-rearrangement sequence a carbamate (compound 11a) and/or an amine (compound 11b) will result, having the greatly reduced $\Delta\sigma_p$ values of 0.35 and 0.2, respectively; thus, the dye-like character of the original sensor will have been dramatically reduced. In cases in which formation of compound 11b can be favored, the effect will be to have converted a dye to a non- or lesser dye.

Variants of the dye-to-non-dye strategy include incorporation of tethering groups to polymers and to metals in a manner analogous to compounds 9 and 10 (See, Scheme 8). The tethering groups may be conveniently incorporated as part of the initial amine (i.e., replacing R and/or R'), but can of course be attached to other loci of the detection portion of the molecule.

Other Sens$_{mod}$ Devices Based on Azo Dye Frameworks

The examples given in Scheme 8 were chosen, to a certain extent, for the sake of simplicity of illustration. It should be obvious to one skilled in the art that virtually any azo dye skeleton could be employed for a Sens$_{mod}$ device. For example, in any known azo dye which possesses an amine/substituted amine, or phenol donor atom, if that atom is replaced by a hydroxamic acid, then a detection device will result that exhibits an increase in $\lambda_{max}$ upon exposure to a nerve agent. Four specific examples of detection systems are shown in Scheme 9 that are analogous to the general systems discussed in Scheme 8. These compounds offer the virtue of superior spectral characteristics due to the presence of the phenol (which typically provides an increase in $\lambda_{max}$ to azo dyes when positioned in such a way that it can form an intramolecular hydrogen bond with the azo group), as well as the virtue of straightforward synthesis. Compound 12 is a simple version of the invention that possesses significant water solubility due to the carboxylate incorporated onto the dye framework. Compound 12 is also an example of a sensor molecule in which the dye characteristics modify with a shift of $\lambda_{max}$ to lower wavelengths upon reaction-rearrangement sequence taking place under most normal conditions (e.g., pH>6). This is because in sensor molecule 12 the distal ends of the chromophore are terminated by a carboxylate and a carboxyamide-like group having approximate Hammett σ values of −0.1 and 0.36, respectively, giving a difference in Hammett σ values of roughly 0.46. After the reaction-rearrangement sequence, depending on whether an amide or amine product results, the electron withdrawing hydroxamic acid is transformed to either a mildly electron donating amide nitrogen (σ=−0.15) or a strongly electron donating amino group (σ=−0.30), giving differences in the σ values of either 0.05 or 0.2, respectively; thus, the chromophore has become less polarized as a consequence of interaction with the nerve agent, and a decrease in $\lambda_{max}$ is expected.

Compound 13 is a polymer bound version of the invention. Compound 14 will attach itself to silver or gold colloids with spontaneous loss of the S-benzyl protecting group. Compound 15 is analogous to compound 12 in that it will have a high degree of water solubility due to negative charge, but becomes a better dye upon exposure to a nerve agent.

Scheme 9. Specific examples of various embodiments of azo dye based Sens$_{mod}$ devices.

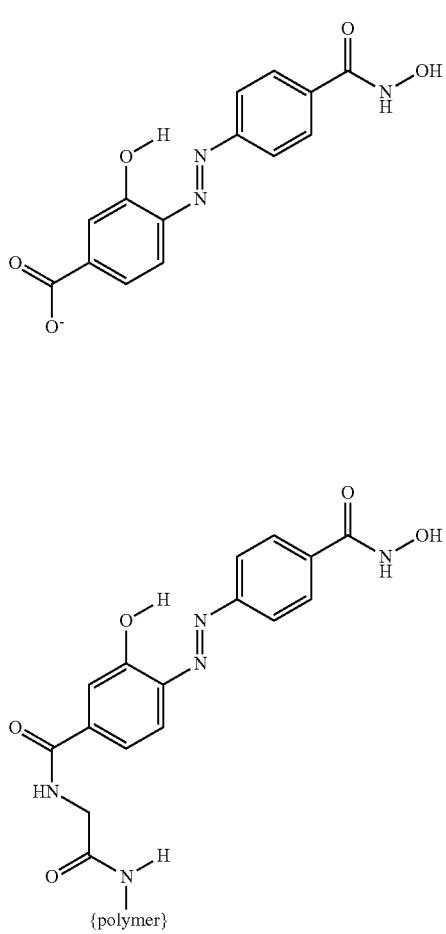

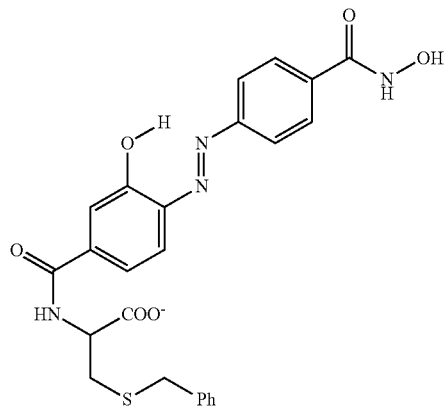

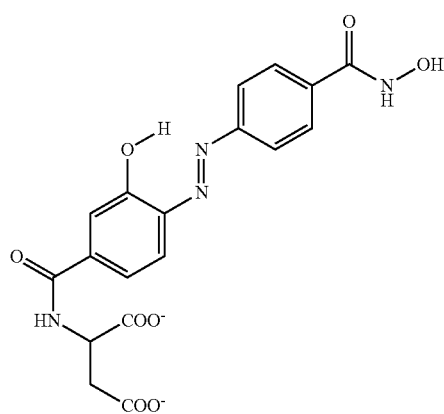

Other Dye Frameworks for Use in the Sens$_{mod}$ Strategy for Nerve Agent Detection The examples given above have focused on azo dyes as the π-systems that are modified by the nerve agent initiated reaction-rearrangement sequence. Given the broad applicability of the principle that the $\lambda_{max}$ of most dyes increase when there is a substantial disparity between the donor/acceptor characteristics of substituents at the ends of conjugated π-systems, it should be obvious that other dyes can be used as the basis of the Sens$_{mod}$ detection devices.

Triarylmethane Dyes. One class of dyes that is an attractive target as the product of the nerve agent initiated reaction-rearrangement sequence are the triarylmethanes. Scheme 10 provides an illustration of operation of two triarylmethane variants of the Sens$_{mod}$ invention. In Scheme 10, "EDG" refers to an electron donating group. Compound 16 of Scheme 10 represents one embodiment of the Sens$_{mod}$ invention that forms such a dye. A key aspect of this embodiment is that while there is little difference between the spectral properties of 4,4'-bis-dialkylaminotriarylmethane dyes and the corresponding 4,4',4"-tris-dialkylaminotriaryl-methanes, the corresponding singly substituted 4-dimethylaminotriarylmethane compounds do not have what are considered to be dye-like properties under common pH conditions (e.g., pH 4-10); in other words, if one has three aryl groups attached to a carbocation the molecule will show dye-like characteristics if two, or if three of the aryl rings have electron donating dialkylamino groups, but not if only one of the rings has an electron donating group. The same principle holds true when the amino/dialkyl-amino groups are replaced by hydroxyl groups (assuming that the pH is sufficiently high, typically above 8), which is the basis for the operation of compound 17 of Scheme 10. Thus, reaction of compound 16 with a nerve agent XYP(O)MLG will result in a Lossen rearrangement and formation of a carbamate or amine product that has strong donors on each of two of the three aromatic rings of the triarylmethane system. Spontaneous solvolysis will occur to provide a dye, 16', related to Malachite Green (see 3c, Scheme 6). Similarly, reaction of 17 with a nerve agent will provide a dye molecule (17') having one hydroxyl and one nitrogen donor atom.

bamate and amine) product is shown in each case. It is obvious to one familiar with the art that considerations described above with respect to detection methods for the reaction-rearrangement sequence, as well as with respect to tether groups for attachment to polymers or metal surfaces apply to these compounds.

Scheme 10: Operation of two triarylmethan variants of the $Sens_{mod}$ invention.

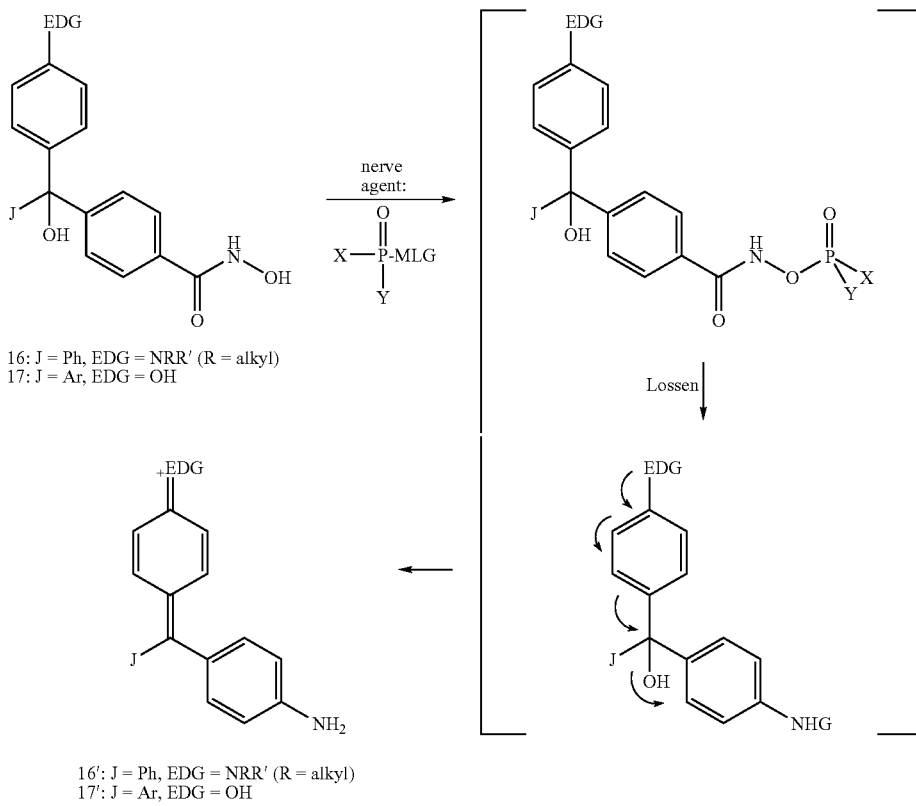

It is obvious that the same considerations with respect to detection (visual and instrumental), as well as advantageous aspects of modifying the dye structures to allow for attachment to polymers or metal surfaces apply to the triarylmethane variants of the $Sens_{mod}$ invention. There are numerous possibilities for attachment of tethers in these systems (such tethers having the same general characteristics as those discussed above for compounds 9 and 10 of Scheme 8), including attachment to the donating amine in compound 16, or especially to the third aromatic ring that is shown as unsubstituted in compounds 16 and 17.

Heterocyclic Dyes. There are several classes of heteroanthracene compounds that provide suitable sensor molecules for the $Sens_{mod}$ strategy. In most cases the products of the reaction-rearrangement sequence will be fluorescent, making fluorescence spectroscopy particularly useful for detection of this nerve agent initiated process, though UV-Vis, IR, Raman and visual detection methods may also be quite effective. The number of these compounds is sufficiently great that possible sensors and the products that would result from a reaction-rearrangement sequence are simply illustrated in Scheme 11. Scheme 11 provides examples of heteroanthracene based variants of the $Sens_{mod}$ invention. Although only amine products are shown in Scheme 11, carbamate products may also be formed. For simplicity, only the amine (rather than the car- Use of Oximes or Oximates in the $Sens_{mod}$ Invention There may be instances in which hydroxamic acids are undesirable for some reason (e.g., they may be less synthetically accessible in some systems). Oximes or the corresponding oximate salts may serve the basis of sensor compositions of the present invention. When oximes or their salts are used, the product of the reaction will be an amide, as opposed to an amine.

Scheme 11. Examples of heteroanthracene based variants of the $Sens_{mod}$ invention.

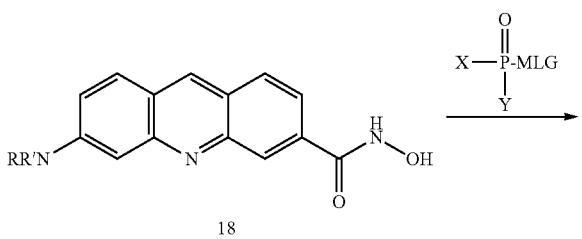

-continued

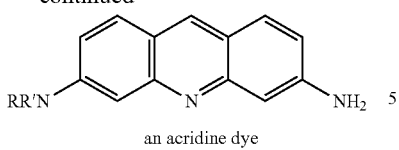
an acridine dye

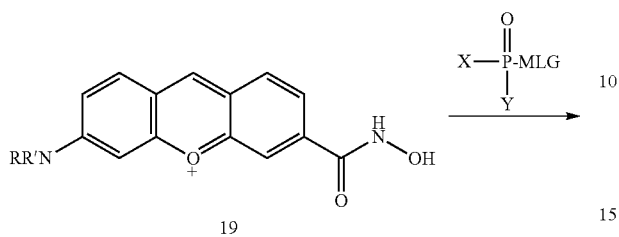
19

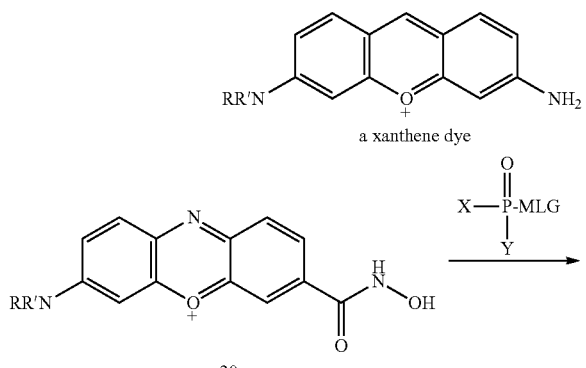
a xanthene dye

20 an oxazine dye

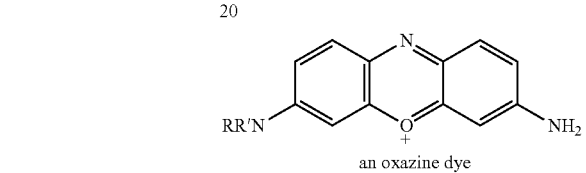
21 a thiazine dye

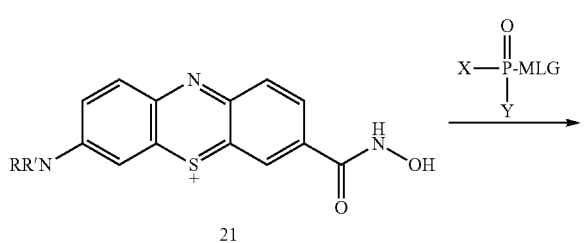
22

-continued

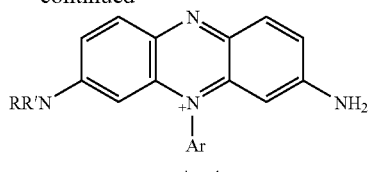
an azine dye

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COON) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting" of may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

EXAMPLE 1

Synthesis of a $Sens_{mod}$ Variant of the Nerve Agent Detection System Based on an Azo Dye: Compound 12

Scheme 12: Synthesis of a sensor composition for the $Sens_{mod}$ Embodiment of the Present Invention (Compound 12).

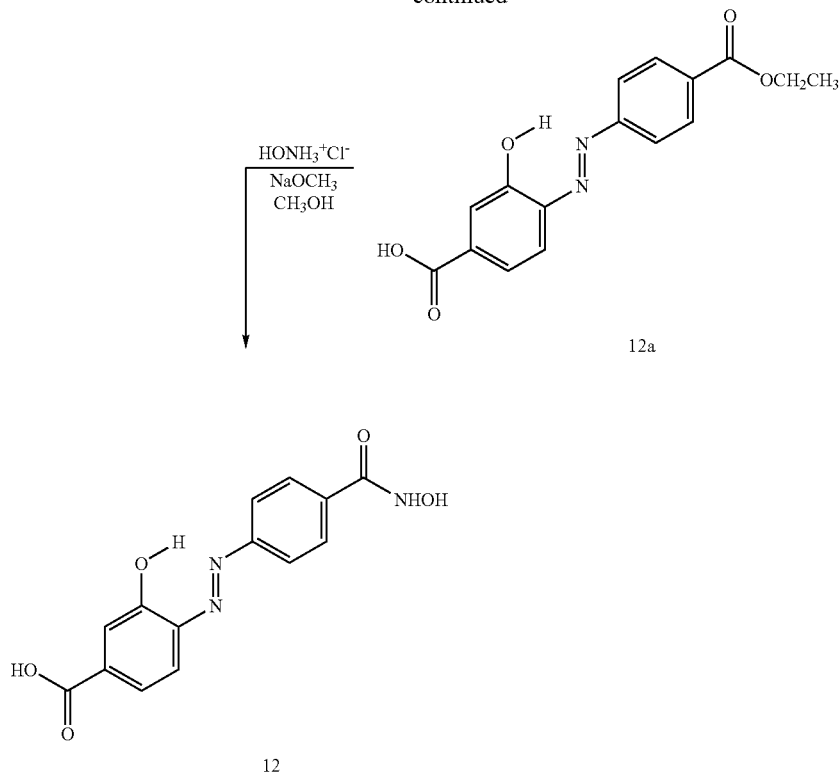

12a

12

Ethyl 4-aminobenzoate (3.30 g) was dissolved in aqueous fluoboric acid (48%, 5 mL) and cooled in an ice/water bath, whereupon it partially precipitated. To the rapidly stirred ice-cold solution was added an ice-cooled solution of sodium nitrite (1.52 g) in water (5 mL), in a dropwise fashion, to give a foamy mixture. After addition was complete, stirring was continued for fifteen minutes and then the mixture filtered through a glass frit, and the precipitate washed with small amounts of ice cold water and then ethyl acetate to give crude the tetrafluoroborate salt of ethyl 4-diazoniumbenzoate. A solution of 3-hydroxybenzoic acid (3.04 g) in saturated aqueous sodium bicarbonate (30 mL) was cooled in ace water and the diazonium salt added in portions, giving immediate formation of a bright orange foamy precipitate. After completion of the addition, the cooling bath was removed and stirring continued for 20 minutes. The solution was transferred to a 2 L Erlenmeyer flask and the solution acidified to pH 4 with concentrated hydrochloric acid. The mixture was filtered through a glass frit and the precipitate washed with cold water to give a bright orange solid that still retained considerable water. This solid (ester acid 12a) was dried first by several repetitions of addition of acetonitrile followed by rotary evaporation, and finally by dissolving a gram in 60 mL dry THF, stirring over anhydrous sodium sulfate, filtration, and concentration by rotary evaporation. Failure to sufficiently dry this material results in poor yields in the subsequent formation of hydroxamic acid.

4-(2-hydroxy-4-carboxyphenyl)azobenzhydroxamic acid (12)

To a solution of sodium methoxide in methanol (1 mL of a 3M solution) in a 10 mL roundbottomed flask was added hydroxylamine hydrochloride (0.139 g), followed by methanol (2 mL). To the resulting mixture was added 4-(4-carbomethyoxyphenylazo)-3-hydroxybenzoic acid (12a, 0.313 g). After stirring for approximately one minute and additional portion of sodium methoxide solution (1 mL of a 3 M solution) was added. The flask was sealed, and the mixture stirred eighteen hours. After dilution with water (25 mL) the mixture was made acidic with concentrated hydrochloric acid to produce a foamy orange precipitate. This was centrifuged and the supernatant removed. The resulting solid was washed several more times using this procedure, and finally the solid was washed with a small amount of acetone to give the target sensor molecule.

Utilization of Sensor Molecule 12.

The sensor molecule (0.0026 g) was dissolved in MOPS buffer (1 mL of 0.13 M 3-(N-morpholino)propanesulfonic acid that had been adjusted to pH 7.7) and 0.5 mL of the resulting solution was transferred to an analysis vial. After recording the Raman spectrum from 400-2800 cm$^{-1}$ the nerve agent simulant diisopropyl fluorophosphate (~1 µL) was added and the spectrum was recorded again at two minute intervals. A time dependent decrease in a peak at ~1400 cm$^{-1}$ was observed (See, FIG. 1 for Raman spectra before, and three minutes after addition of the nerve agent simulant diisopropyl fluorophosphate).

EXAMPLE 2

Synthesis of a $Sens_{mod}$ Variant of the Nerve Agent Detection System Based on an Azo Dye: Compound 15

Scheme 13: Synthesis of a sensor composition for the $Sens_{mod}$ Embodiment of the Present Invention (Compound 15).

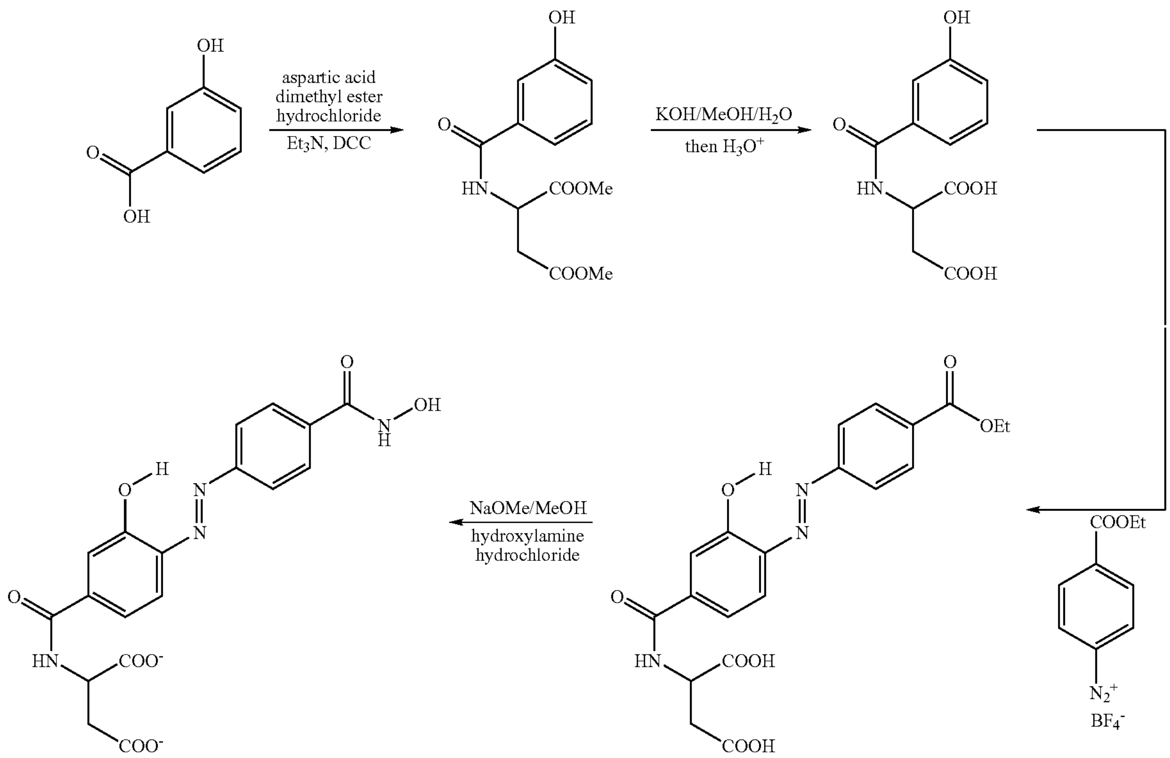

15

Scheme 13 illustrates a synthetic pathway for making sensor composition 15 for the $Sens_{mod}$ embodiment of the present invention. To a 25 mL roundbottom flask containing a magnetic stir bar is added m-hydroxybenzoic acid (0.661 g, 4.8 mmol) and aspartic acid dimethyl ester hydrochloride (0.994 g, 5.0 mmol, 1.05 equiv). To the mixture is added freshly distilled (from potassium) THF, followed by distilled (from $CaH_2$) triethylamine (0.8 mL, 5.7 mmol, 1.2 equiv). The flask is sealed with a septum, stirred approximately five minutes, and then the flask unsealed and dicyclohexylcarbodiimide (1.567 g, 7.6 mmol, 1.6 equiv) added in one portion. The flask is resealed and the mixture stirred 15 hours. The mixture is transferred to a separatory funnel with dichloromethane (80 mL) and washed with 1 M hydrochloric acid (2×25 mL), saturated aqueous sodium bicarbonate (2×20 mL) and brine (1×10 mL). The organics are dried by stirring approximately one hour over sodium sulfate, then filtered and concentrated by rotary evaporation. After purification by flash chromatography, an 0.2 M solution of the purified diester in methanol is saponified with six molar equivalents of sodium hydroxide (introduced as a 1 M aqueous solution) by stirring for 24 hours under nitrogen. Removal of the methanol is followed by dilution with water (20 mL), acidification to pH 2 with concentrated hydrochloric acid, and extraction with ethyl acetate (3×20 mL). The combined organic extracts are washed with brine (1×15 mL), dried over sodium sulfate, and concentrated. The crude product so obtained is treated with 1.1 molar equivalents of the known diazonium tetrafluoroborate of ethyl 4-aminobenzoate in 2:2:1 methanol/water/sat'd sodium bicarbonate (10 mL). After rotary evaporation to remove the bulk of the methanol, the mixture is acidified to pH 3, saturated with sodium chloride, and extracted with ethyl acetate (3×20 mL). After washing with brine (1×15 mL) the organics are dried ($Na_2SO_4$), filtered, and rotary evaporated. The crude product so obtained is treated with two molar equivalents hydroxylamine hydrochloride and eight equivalents sodium methoxide in methanol (as a 3 M solution). After stirring 14 hours the mixture is diluted with water (50 mL), the pH adjusted to roughly 3, and the mixture extracted with ethyl acetate (3×30 mL) and the organics washed with brine (1×20 mL). After drying over sodium sulfate, the solvents are removed by rotary evaporation to yield the target sensor compound 12. Dissolution of compound 12 in pH 7.8 buffer to give a 0.001 M solution may be followed by addition of diisopropyl fluorophosphate (or Sarin), resulting in marked changes in the UV-Vis spectrum.

EXAMPLE 3

Synthesis of a Xanthene Variant of the $Sens_{conj}$ Invention: (Compound 1')

Scheme 14: Synthesis of a sensor composition for the $Sens_{mod}$ Embodiment of the Present Invention (Compound 1').

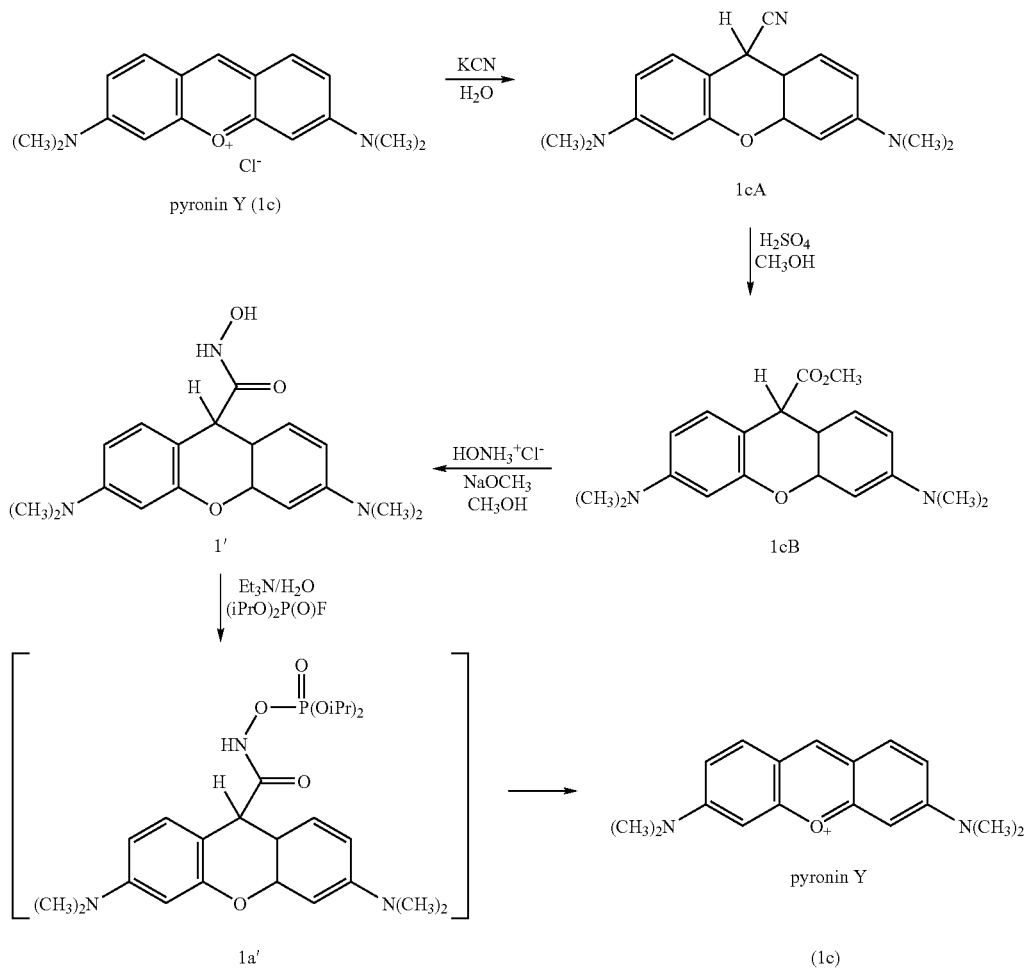

N,N,N'N'-tetramethyl-9-cyano-9H-xanthene-2,6-diamine (1cA). Pyronin Y (0.90 g, ca. 50% dye content) was dissolved in water (12 mL) by heating, and the supernatant decanted into a 50 mL round bottom flask. To the vigorously stirred solution was added a solution of potassium cyanide (0.90 g) in water (9 mL). The flask was immersed in a 65-70° C. oil bath and stirred for 0.5 hour. The hot solution was then filtered through a sintered glass funnel and the precipitate washed with water to yield a brownish powder (0.42 g) that appeared to be of high purity on the basis of $^1$H NMR, and which was used directly in the next reaction. $^1$H NMR (CDCl$_3$): δ7.265 (d, 8.8 Hz, 2H), 6.522 (dd, 8.8 Hz, 2.4 Hz, 2H), 6.395 (d, 2.4 Hz, 2H), N,N,N'N'-tetramethyl-2,6-diamino-9H-xanthene-9-carboxylic acid methyl ester (1cB) Sulfuric acid (1.5 mL) was added to methanol (1.5 mL), and the hot mixture was added to a portion of the crude nitrile 1cA (0.10 g) in a nitrogen flushed 25 mL round bottom flask containing a magnetic stirbar. A condenser was attached to the flask, which was then heated at reflux under nitrogen in a 90° C. oil bath for 2.5 hour.

After cooling, saturated potassium carbonate was cautiously added to give pH 9. The resulting mixture was extracted three times with ethyl acetate and the organic extracts dried over sodium sulfate. After filtration, the solvent was removed by rotary evaporation to give the crude ethyl ester (0.070 g). Chromatography on a 0.75"×4.5" of silica gel using 3% ethyl acetate in dichloromethane afforded pure product (0.035 g).

N,N,N'N'-tetramethyl-2,6-diamino-9Hxanthene-9-hydroxamic acid (1') The methyl ester 1cB (0.039 g) was combined with hydroxylamine hydrochloride (0.010 g) in a 3 mL vial. Addition of methanol (2 mL) gave a purple solution. Subsequent addition of sodium methoxide (0.2 mL of a freshly prepared 3 M solution in methanol) led to a colorless solution that was stirred overnight under nitrogen. After rotary evaporation of the methanol, water (ca. 2 mL) was added, and the pH of the mixture was adjusted to approximately 6 with sulfuric acid. The resulting solution was extracted with ethyl acetate (3×2 mL), and the organic extracts dried (sodium sulfate), filtered, and concentrated by rotary evaporation to give a substantially pure product (0.024 g) that was very light purple in color, and suitable for use in the detection of nerve agents.

Utilization of the Sensor Molecule 1'

Figure 2:
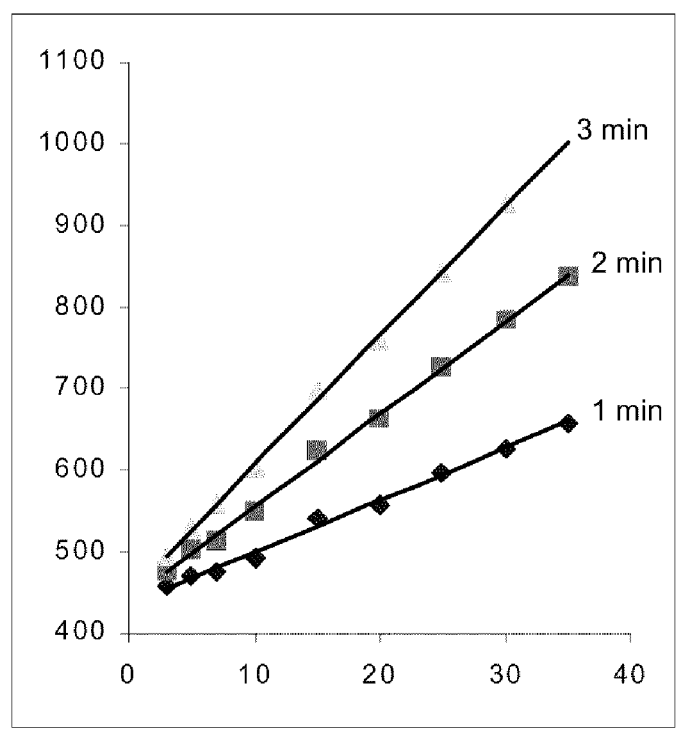
FIG. 2 shows fluorescence emission intensities as a function of DIFP concentration (in units of $10^{-6}$ M) at 1, 2 and 3 minute reaction times following addition of DIFP to a $10^{-5}$ M solution of 1' in 0.0025 M aqueous triethylamine.

The sensor 1' (0.0032 g) was dissolved in methanol (2.5 mL) to give a roughly 4 mM solution. A portion of this methanolic sensor solution (0.200 mL) was added to aqueous triethylamine (40 mL of an 0.0025 M solution), and the resulting stock analysis solution was divided into 2 mL aliquots. Addition of varying concentrations of stock solutions of the nerve agent simulant diisopropyl fluorophosphate (in 10 μL portions) was followed fluorescence measurement (excitation at 540 nm, emission recorded at 562 nm) at a fixed time period. With final nerve agent simulant concentrations of 3, 5, 7, 10, 15, 20, 25, 30 and $35 \times 10^{-6}$ M and fluorescence measurements taken at 1, 2 and 3 minute intervals, the calibration curves shown in FIG. 2 were produced. Utilization of the sensor molecule with nerve agents will produce qualitatively similar results.

Visual Detection of Nerve Agents Using the Sensor Molecule 1'

Figure 3:
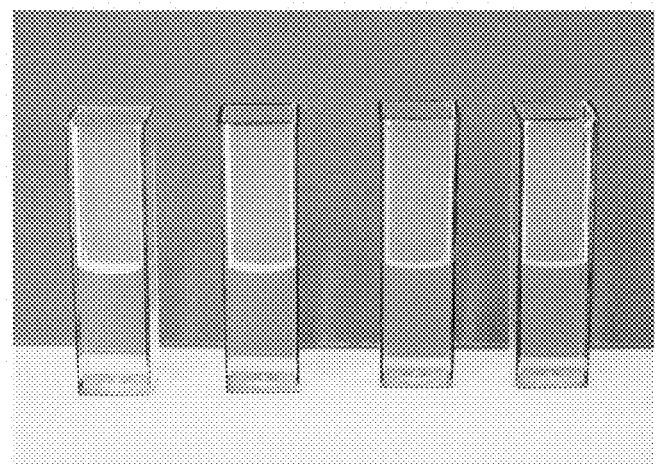
FIG. 3 provides images of cuvettes containing 0.01 M Et$_3$N, $10^{-5}$ M 1' and (left to right) 0, 7, 21 and $63 \times 10^{-4}$ DIFP, corresponding to 0, 100, 300 and 900 ppm sarin. The photograph was taken approximately 1-2 minutes after addition of the nerve agent simulant to the analysis solutions.

A stock solution of sensor molecule 1' ($1 \times 10^{-5}$ M in 1' and 0.01 M in triethylamine) was divided amongst four cuvettes and diisopropyl fluorophosphates (DIFP) added to give final concentrations of 0, 7, 21 and $63 \times 10^{-4}$ DIFP, corresponding to 0, 100, 300 and 900 ppm sarin. A photograph taken approximately 1-2 minutes after addition of the nerve agent simulant to the analysis solutions is shown in FIG. 3, and demonstrates that the various levels of simulant can be visually differentiated.

Specificity of the Sensor Molecule 1' for Good Nerve Agent Simulants.

Figure 4:
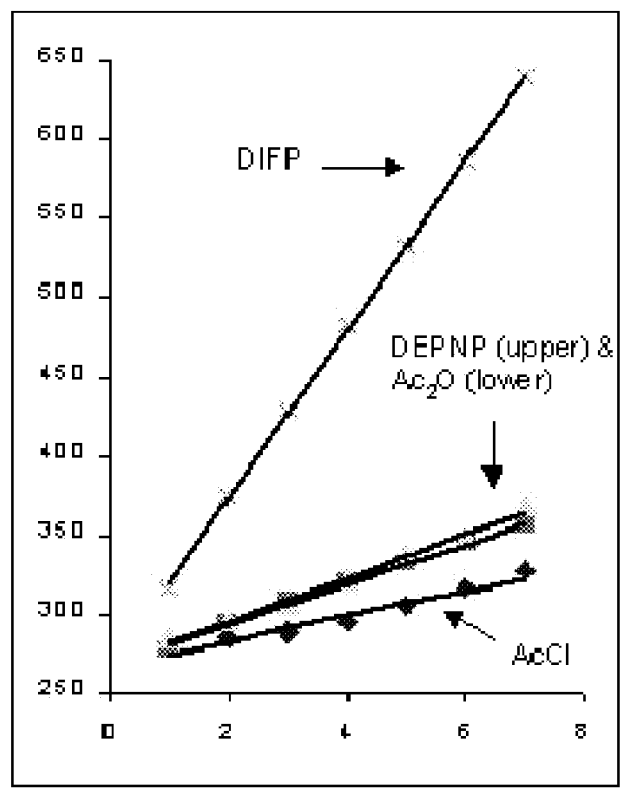
FIG. 4 provides a graph showing time dependence of fluorescence intensities on combining compound 1' and triethylamine with solutions containing $25 \times 10^{-6}$ M DIFP, diethyl p-nitrophenyl phosphate (DEPNP), acetyl chloride and acetic anhydride.

As discussed above, the selectivity of these new variants of the original assay relies on the particular reactivity that hydroxamic acids show towards phosphorylating agents, as well as a subsequent rearrangement reaction that is characteristic of O-phosphoryl derivatives of the hydroxamic acids. It was expected that carboxylic acid derivatives would not give a detectable response, since it is well known that the Lossen rearrangement typically requires either very high temperatures (the term commonly used being "destructive distillation"), or formation of salts of the O-acyl hydroxamates, followed by thermolysis at lower temperatures. FIG. 4 provides a graph showing time dependence of fluorescence intensities on combining compound 15 and triethylamine with solutions containing $25 \times 10^{-6}$ M DIFP, diethyl p-nitrophenylphosphate (DEPNP, a nerve agent simulant that is safer than DIFP though less effective a simulant because of its lower reactivity), acetyl chloride and acetic anhydride. The plots are normalized to a common starting fluorescence intensity. To simulate a scenario in which a water supply is attacked, measurements were taken by adding the compound of interest to water, waiting thirty minutes, and then adding sensor solution (15 and triethylamine) to give the appropriate final concentrations. As can be seen from these results, expectations with respect to the behavior of the sensor with a good nerve agent simulant (DIFP) and a mediocre nerve agent simulant (DEPNP) were entirely fulfilled; the former reacts quite quickly, while the latter is fairly slow.

In a separate set of experiments to examine compounds that have acted as interferents in a variety of assays (test strip, ion mobility spectrometry, surface acoustic wave spectrometry), 12 N HCl, phosphoric acid (acids are interferents in a variety of assays), acetic acid, hydrolyzed diethyl chlorophosphate, malathion (a pesticide giving false positives with some commercial test strips) and dimethyl methylphosphonate (an interferent that reportedly gives false positives in ion mobility spectroscopy), and DIFP were added to analysis solutions to give 50-60 parts per thousand concentrations (i.e., 1000-fold higher concentrations than necessary to detect DIFP). The DIFP gave instantaneous coloration; however, even after three hours, none of the other samples showed any sign of color (the malathion showed a faint pink tinge after roughly 17 hours; the others remained colorless).

These results demonstrate the capability of sensor compound 1' to readily differentiate between good simulants (or nerve agents) and poor simulants. Although acetyl chloride and acetic anhydride showed produced a response with the sensor compound, the response was much lower than that to good simulants (or nerve agents), and this slower/lower rate of response could be used to distinguish these compounds from actual threats. The fact that these compounds react at all with the sensor may be attributed to the extraordinarily high migratory aptitude of the reporter portion of 1' (See, Jones, L. W. and Hurd, C. D., *Journal of the American Chemical Society*, 1921, 43, 2422-48). The facts that acetic anhydride and acetyl chloride are not commonly encountered substances outside a specialized chemical laboratory, and that they are distinguishable from true nerve agents/good simulants on the basis of the intensity and rates of reactions mean that for most purposes the response of the sensor to these compounds does not pose a problem. However, if the user prefers to have a detection system that has an even higher level of selectivity towards nerve agents, the use of $Sens_{mod}$ variants of the invention will provide this, since the migratory aptitude of the aryl groups that will most commonly be employed in such embodiments is much, much lower than the reporters used in the $Sens_{conj}$ embodiments.

Utilization of Sensor Composition 1' with Raman Detection

The reaction-rearrangement product formed by treatment of $10^{-5}$ M solutions of sensor composition 1' in 0.0025 M aqueous triethylamine is detected with a very high degree of sensitivity in the presence of colloidal silver using surface enhanced Raman scattering (SERS) spectroscopy employing a HeNe laser (though other Raman systems could, of course be used). This is due, in part, to the spectral characteristics of the sensor molecule, since its chromophore has substantial overlap with the HeNe laser line. In addition, the interaction of the sensor with nerve agent is sensitively detected because the product resulting from the reaction-rearrangement reaction is adsorbed very effectively by the silver surface, leading to a large SERS enhancement. In fact, this strong affinity of the reaction rearrangement product with the silver surface can be associated with a difficulty that may be experienced when using this spectroscopic method with the sensor composition. Unless the sensor composition is of extremely high purity, an impurity resulting from air/light mediated oxidation of the sensor that has a SERS spectrum very similar to that of the reaction-rearrangement product, and which has a very high affinity for the silver surface, will produce a very large background signal that may interfere with high sensitivity measurements of nerve agent.

EXAMPLE 4

Synthesis of Triarylamine Variants of the $Sens_{conj}$ Invention: Compound 3 and its Hydroxamic Acid Variant 3'

Scheme 15 provides a schematic diagram illustrating a synthetic pathway for making Triarylamine sensor compounds for use in the $Sens_{conj}$ embodiment of the present invention.

Scheme 15: An illustration of the synthesis of compound 3 and its hydroxamic variant 3'.

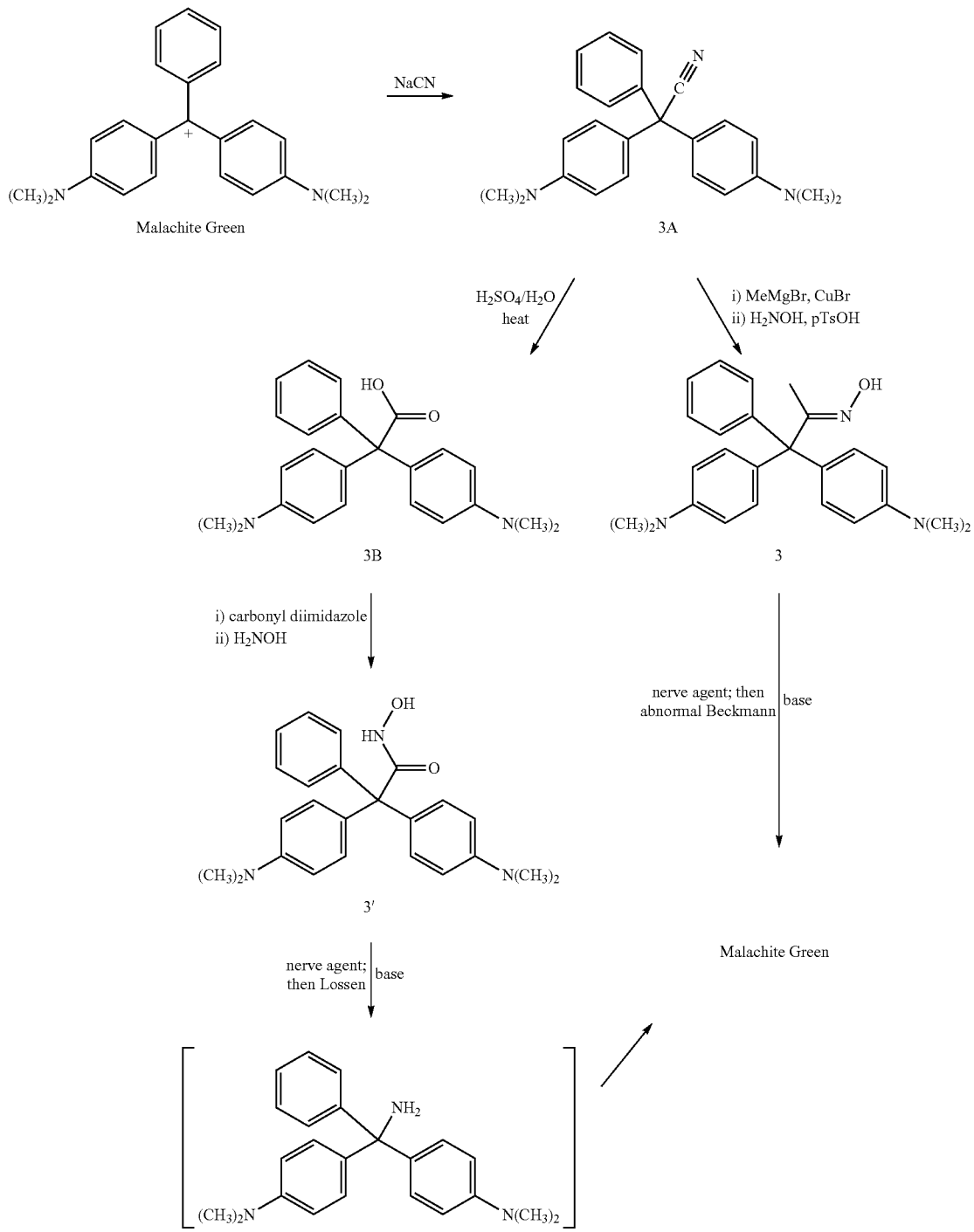

α,α-bis(4-dimethylaminophenyl)phenylacetonitrile (3A)

Commercially obtained Malachite Green, oxalate salt (4.644 g) and sodium cyanide (2.456 g) were combined, followed by addition of water (150 mL) and diethyl ether (150 mL). The mixture was rapidly stirred for three hours, at which point the green color had faded, and the mixture was a muddy brown. The mixture was transferred to a separatory funnel with the aid of ethyl acetate, partitioned, and the aqueous phase extracted with three portions of ethyl acetate (100 mL each). The combined organics were washed once with brine (50 mL), dried over sodium sulfate, filtered and concentrated by rotary evaporation to provide crude nitrile 3A contaminated by some of the triarylcarbinol.

2,2-bis(4-dimethylaminophenyl)-2-phenyl2-propanone oxime (3)

This compound is prepared by a variation in the procedure of Weiberth and Hall (Weiberth, F. J. and Hall, S. S., *Journal of Organic Chemistry* 1987, 52, 3901-04). Chromatographed nitrile 3A (0.71 g) is combined in an oven dried flask with a solution of methyl magenesium bromide in THF (1.1 mL of a 2 M solution). Dried cuprous bromide (~0.008 g) is added and the mixture heated to reflux under nitrogen for 14 hours, at which point the reaction is cooled, first to room temperature, and then in ice/water. Dry methanol (0.5 mL) is cautiously added, followed by a solution of freshly distilled hydroxylamine (~0.6 g) and p-toluenesulfonic acid (0.86 g) in methanol. The mixture is stirred for 48 hours, then refluxed for four hours. After cooling to room temperature the mixture is diluted with 50 mL water, the pH adjusted to ~5, and the mixture extracted with ethyl acetate (3×25 mL). The combined organics are washed with brine (20 mL), dried (sodium sulfate), filtered, and concentrated by rotary evaporation.

α,α-bis(4-dimethylaminophenyl)phenylacetic acid (3B)

The target acid is not readily chromatographed. To obtain pure acid it is easiest to hydrolyze the crude nitrile to crude acid, convert the acid to the readily chromatographable methyl ester, and then hydrolyze this ester back to the acid. Crude nitrile 3B was added to a hot, freshly prepared mixture of sulfuric acid (18 mL) and water (12 mL). After attaching a condenser to the flask, the mixture was placed in a preheated oil bath and refluxed 1.5 hours. After cooling to room temperature, the dark mixture was poured into water (100 mL), along with two rinses of the reaction flask (20 mL each). The pH of the mixture was adjusted to approximately 5 with sodium hydroxide pellets while cooling the flask in ice/water (substantial amounts of precipitated sodium sulfate appears). The mixture was extracted repeatedly with ethyl acetate (1×100 mL, 3×50 mL) and the combined organics washed once with brine (50 mL), dried (sodium sulfate) and concentrated to give crude acid (~1.1 g) that was used directly in the next reaction. The crude acid was dissolved in dry THF and sodium hydride was added (0.288 g of a 60% oil dispersion). After some of the foaming had abated (~5 min), dimethyl sulfate (0.35 mL) was added, the flask sealed, and the mixture stirred approximately 18 hours. After dilution with ethyl acetate (80 mL) the mixture was washed with 1:1 water/brine (20 mL) and then brine (20 mL). The organics were dried (sodium sulfate), filtered, and concentrated by rotary evaporation to give ~1.1 g crude ester that was chromatographed to obtain pure product (~0.54 g, Rf 0.6 with 30% ethyl acetate/hexanes on Merck 0.25 mm Silica Gel 60 TLC plates). In contrast to the various impurities present in the crude mixture, the spot corresponding to the ester does not become green/blue upon exposure to UV light, but rather becomes slightly yellowish. The pure ester (0.196 g) was added to a hot, freshly prepared 1:1 mixture of concentrated sulfuric acid and water (12 mL) and heated at reflux for 1.5 hours. After cooling, the mixture was added to cold water (60 mL), along with two washes of the reaction vessel (2×10 mL). The aqueous was adjusted to slightly above pH 5 and extracted with ethyl acetate (2×75 mL); this extraction procedure was repeated after readjusting the pH to slightly less than 6, and slightly less than 5. The combined organics were washed with brine (50 mL), dried (sodium sulfate), and concentrated by rotary evaporation. On TLC the product is initially colorless, but appears as a blue streak after exposure to UV radiation.

α,α-bis(4-dimethylaminophenyl)phenylacetohydroxamic acid (3')

Dry THF (2 mL) was added to acid 3B (0.082 g), and the mixture stirred under nitrogen for 10 minutes. Carbonyl diimidazole (0.078 g) was added, leading to gas evolution and formation of a homogeneous solution. Freshly distilled, crystalline hydroxylamine (cf. *Inorganic Syntheses*, vol. 1, page 87) was added and the mixture stirred for 1.5 hours, at which point the flask was immersed in a ~40° C. water bath for about ten minutes. After cooling to room temperature, the mixture was diluted with ethyl acetate (30 mL), washed with water (2×5 mL), dried (sodium sulfate), filtered and concentrated by rotary evaporation. The product is almost insoluble in water. When a $10^{-4}$ M solution in 3:1:4 methanol/THF/water is prepared and treated with an equimolar amount of DIFP, no pronounced color change is noted, presumably because the reaction-rearrangement product does not solvolyze under these relatively non-polar conditions. However, addition of a drop of concentrated hydrochloric acid produces a green coloration.

We claim:

1. A compound for sensing phosphorus based nerve agents having the formula:

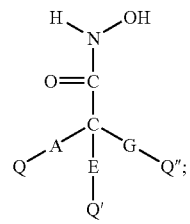

or having the formula:

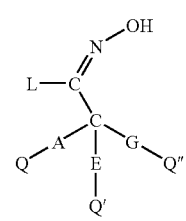

or a salt, or an enantiomer thereof; wherein:

L is an alkyl group or an aryl group;

A is a conjugated π-system that comprises at least four atoms selected from the group consisting of carbon and nitrogen;

E comprises at least two atoms selected from the group consisting of carbon and nitrogen that are doubly or triply bonded to each other;

G is hydrogen, alkyl, aryl, heteroaryl, alkenyl, alkynyl, halide, alkoxyl, aryloxyl, aroyloxyl, alkyl- or aryl- or dialkyl- or diaryl- or alkylarylamino, thioalkyl, or thioaryl; and Q, Q' and Q" are independently halogen, —H, —OR, —SR, —NRR', —C(O)R, —C(O)H, —COOR, —CN, —CR═NR', —C(O)NRR', —NO$_2$, —NO, —N═NR, —N$^+$RR'R", —S(O)R, —SO$_2$R, —SO$_3^-$, —P(O)(OR)(OR'), or —P(O)(NRR')OR", in which R, R' and R" are independently —H, alkyl, aryl or any combination of these.

2. The compound of claim 1 wherein A is selected from the group consisting of an aromatic ring, a substituted aromatic ring, a heteroaromatic ring and a substituted heteroaromatic ring.

3. The composition of claim 1 wherein E comprises between two to thirty atoms chosen from carbon or nitrogen having sp or sp$^2$ hybridization that are in an uninterrupted sequence such that each atom is adjacent to at least one other in the sequence, and possessing geometries about each atom that allows for substantial overlap of a p-orbital of one atom with an adjacent member of the two to thirty atoms, thereby forming a conjugated π-system.

4. The composition of claim 1 wherein Q, Q', Q" or any combination of these is attached to a solid support selected from the group consisting of silica gel, glass, polymers, and metal.

5. A compound for sensing phosphorus based nerve agents having the formula:

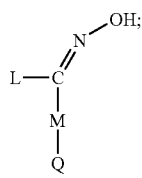

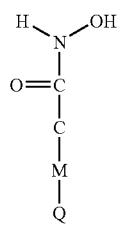

or a salt, or an enantiomer thereof; wherein:

L is an alkyl group or an aryl group;

M is selected from the group consisting of an aromatic ring, a substituted aromatic ring, a heteroaromatic ring and a substituted heteroaromatic ring; and Q is halogen, —H, —OR, —SR, —NRR', —C(O)R, —C(O)H, —COOR, —CN, —CR=NR', —C(O)NRR', —NO$_2$, —NO, —N=NR, —N$^+$RR'R", —S(O)R, —SO$_2$R, —SO$_3^-$, —P(O)(OR)(OR'), or —P(O)(NRR')OR", in which R, R' and R" are independently —H, alkyl aryl or any combination of these.

6. The composition of claim 5 wherein Q is attached to a solid support selected from the group consisting of silica gel, glass, polymers, and metal.

7. The composition of claim 5 wherein M is a derivative of a reporter group selected from the group consisting of azo dyes, xanthene dyes, anthraquinone dyes, acridine dyes, azine dyes, oxazine dyes, thiazine dyes, triarylmethane dyes, diarylmethane dyes, quinolone styryl dyes, phthalocyanine dyes, and polyalkene dyes.

8. The composition of claim 5 wherein M is a derivative of a reporter group selected from the group consisting of rhodamine, fluorescein, neutral red, safranin, Nile Blue, methylene blue, Malchite green, auramine, and carotene.

* * * * *

UNITED STATES PATENT AND TRADEMARK OFFICE
CERTIFICATE OF CORRECTION

PATENT NO. : 7,951,607 B2  
APPLICATION NO. : 12/691636  
DATED : May 31, 2011  
INVENTOR(S) : Corcoran et al.

Page 1 of 1

It is certified that error appears in the above-identified patent and that said Letters Patent is hereby corrected as shown below:

In the Specification:

In claim 5, column 61, lines 12-17, please delete the first structure provided.

In claim 5, column 62, lines 11-12, please replace "alkyl aryl" with --alkyl, aryl--.

Signed and Sealed this  
Fourth Day of October, 2011

David J. Kappos  
*Director of the United States Patent and Trademark Office*